US010919827B2

United States Patent
Werner et al.

(10) Patent No.: US 10,919,827 B2
(45) Date of Patent: Feb. 16, 2021

(54) PROCESS FOR RECOVERING 3-METHYLBUT-3-EN-1-OL

(71) Applicant: BASF SE, Ludwigshafen am Rhein (DE)

(72) Inventors: Albert Werner, Ludwigshafen am Rhein (DE); Miriam Bru Roig, Ludwigshafen am Rhein (DE); Andrei-Nicolae Parvulescu, Ludwigshafen am Rhein (DE); Roland Minges, Ludwigshafen am Rhein (DE); Andreas Keller, Ludwigshafen am Rhein (DE); Stephan Maurer, Ludwigshafen am Rhein (DE); Ulrich Mueller, Ludwigshafen am Rhein (DE); Wolfgang Siegel, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/636,474

(22) PCT Filed: Aug. 10, 2018

(86) PCT No.: PCT/EP2018/071771
§ 371 (c)(1),
(2) Date: Feb. 4, 2020

(87) PCT Pub. No.: WO2019/030386
PCT Pub. Date: Feb. 14, 2019

(65) Prior Publication Data
US 2020/0239394 A1 Jul. 30, 2020

(30) Foreign Application Priority Data
Aug. 11, 2017 (EP) .................................... 17185851

(51) Int. Cl.
*C07C 29/80* (2006.01)
*C07C 29/38* (2006.01)
*C07C 33/025* (2006.01)
*C07C 33/03* (2006.01)
*B01D 3/14* (2006.01)
(Continued)

(52) U.S. Cl.
CPC .............. *C07C 29/80* (2013.01); *B01D 3/143* (2013.01); *B01J 29/7057* (2013.01);
(Continued)

(58) Field of Classification Search
CPC ...................................................... C07C 29/80
See application file for complete search history.

(56) References Cited

U.S. PATENT DOCUMENTS

| 3,574,773 A | 4/1971 | Mueller et al. |
| 2011/0054083 A1 | 3/2011 | Lorenz et al. |
| 2012/0059177 A1 | 3/2012 | Gralla et al. |

FOREIGN PATENT DOCUMENTS

| DE | 1279014 B | 10/1968 |
| WO | WO-02051776 A2 | 7/2002 |

(Continued)

OTHER PUBLICATIONS

Translation of patent No. DE1279014B, Oct. 3, 1968, pp. 1-6 (Year: 1968).*

(Continued)

*Primary Examiner* — Medhanit W Bahta
(74) *Attorney, Agent, or Firm* — Faegre Drinker Biddle & Reath LLP

(57) ABSTRACT

The present invention relates to a process for recovering 3-methylbut-3-en-1-ol from a feed stream F1 comprising 3-methylbut-3-en-1-ol, one or more solvents, water, and isobutene, wherein 3-methylbut-3-en-1-ol, the one or more solvents and water are separated from isobutene by distillation, the process comprising subjecting the feed stream F1 to distillation conditions in a distillation unit, obtaining a bottoms stream B1 which is enriched in -methylbut-3-en-1-ol, in the one or more solvents and in water compared to the feed stream F1 subject The present invention relates to a process for recovering 3-methylbut-3-en-1-ol from a feed stream F1 comprising 3-methylbut-3-en-1-ol, one or more solvents, water, and isobutene, wherein 3-methylbut-3-en- (Continued)

1-ol, the one or more solvents and water are separated from isobutene by distillation, the process comprising subjecting the feed stream F1 to distillation conditions in a distillation unit, obtaining a bottoms stream B1 which is enriched in -methylbut-3-en-1-ol, in the one or more solvents and in water compared to the feed stream F1 subjected to distillation conditions, and a top stream T1 which is enriched in isobutene, further subjecting the bottoms stream B1 to distillation conditions in a second distillation unit and obtaining a bottoms stream B2 which is enriched in 3-methylbut-3-en-1-ol compared to the bottoms stream B1 and a top stream T2 which is enriched in water compared to the bottoms stream B1, further subjecting the bottoms stream B2 to distillation conditions in a third distillation unit and obtaining a top stream T3 which is enriched in 3-methylbut-3-en-1-ol compared to the bottoms stream B2 and a bottoms stream B3. ted to distillation conditions, and a top stream T1 which is enriched in isobutene, further subjecting the bottoms stream B1 to distillation conditions in a second distillation unit and obtaining a bottoms stream B2 which is enriched in 3-methylbut-3-en-1-ol compared to the bottoms stream B1 and a top stream T2 which is enriched in water compared to the bottoms stream B1, further subjecting the bottoms stream B2 to distillation conditions in a third distillation unit and obtaining a top stream T3 which is enriched in 3-methylbut-3-en-1-ol compared to the bottoms stream B2 and a bottoms stream B3.

19 Claims, 2 Drawing Sheets

(51) Int. Cl.
  *B01J 29/70* (2006.01)
  *B01J 37/02* (2006.01)
  *B01J 37/08* (2006.01)
(52) U.S. Cl.
  CPC ......... *B01J 37/0203* (2013.01); *B01J 37/086* (2013.01); *C07C 29/38* (2013.01); *C07C 33/025* (2013.01); *C07C 33/03* (2013.01); *B01J 2229/186* (2013.01); *B01J 2229/37* (2013.01)

(56) References Cited

FOREIGN PATENT DOCUMENTS

| WO | WO-2011147919 A1 | 12/2011 |
| WO | WO-2011154330 A1 | 12/2011 |
| WO | WO-2014060259 A1 | 4/2014 |
| WO | WO-2015067654 A1 | 5/2015 |

OTHER PUBLICATIONS

Fei, Z., "Enhanced activity of MCM-48 based tin catalyst for synthesis of 3-methylbut-3-en-1-ol by adjusting the mesochannel environment", Journal of Industrial and Engineering Chemistry, 2014, vol. 20, pp. 4146-4151.
International Preliminary Report on Patentability for PCT/EP2018/071771 dated Oct. 11, 2018.

* cited by examiner

PROCESS FOR RECOVERING 3-METHYLBUT-3-EN-1-OL

CROSS-REFERENCE TO RELATED APPLICATIONS

This application is a national stage application (under 35 U.S.C. § 371) of PCT/EP2018/071771, filed Aug. 10, 2018, which claims benefit of European Application No. 17185851.7, filed Aug. 11, 2017, both of which are incorporated herein by reference in their entirety.

The present invention relates to a process for recovering 3-methylbut-3-en-1-ol from a feed stream F1 comprising 3-methylbut-3-en-1-ol (MBE), one or more solvents, water, and isobutene, wherein 3-methylbut-3-en-1-ol, the one or more solvents and water are separated from isobutene by distillation, the process comprising subjecting the feed stream F1 to distillation conditions in a distillation unit, obtaining a bottoms stream B1 which is enriched in -methylbut-3-en-1-ol, in the one or more solvents and in water compared to the feed stream F1 subjected to distillation conditions, and a top stream T1 which is enriched in isobutene, further subjecting the bottoms stream B1 to distillation conditions in a second distillation unit and obtaining a bottoms stream B2 which is enriched in 3-methylbut-3-en-1-ol compared to the bottoms stream B1 and a top stream T2 which is enriched in water compared to the bottoms stream B1, further subjecting the bottoms stream B2 to distillation conditions in a third distillation unit and obtaining a top stream T3 which is enriched in 3-methylbut-3-en-1-ol compared to the bottoms stream B2 and a bottoms stream B3. The process further comprises recovering the one or more solvents from the feed stream F1, wherein the one or more solvents is recovered from bottoms stream B3 provided that the one or more solvents have a boiling point higher than 3-methylbut-3-en-1-ol and wherein the one or more solvents is recovered from the top stream T2 provided that the one or more solvents have a boiling point lower than 3-methylbut-3-en-1-ol. The process further comprises recovering isobutene from the top stream T1.

The currently available processes for the preparation of 3-methylbut-3-en-1-ol are carried out in the absence of solvents. A drawback of these processes is that they require at high pressure of more than 250 bar and temperature of more than 250° C.

3-methylbut-3-en-1-ol is an important intermediate in the chemical industry. It has been seen that a process for the preparation of 3-methylbut-3-en-1-ol from isobutene and formaldehyde in the presence of a condensation catalyst comprising a zeolite and which is carried out in the presence of one or more solvents can be carried out at low pressures and low temperature with respect to a process carried out without solvent. Due to its importance for industrial-scale processes, it is desired to carry out this process as efficiently as possible. An efficient process means also the recovery of the valuable product, of the unreacted material and of the solvents in high amount and high purity. The condensation reaction between isobutene and formaldehyde results in a mixture comprising 3-methylbut-3-en-1-ol as the valuable product, solvent(s) and water. Therefore to render the process economically advantageous it is necessary to recover the valuable product and the solvents used in the condensation reaction in high amount and high purity. Further since the condensation is usually carried out with an excess on isobutene, the resulting mixture further comprises varying amounts of isobutene. Especially in industrial-scale continuous processes for the condensation of isobutene in a solvent, one feature of the overall process is the recovery and recycling of the unconsumed isobutene.

It was therefore an object of the present invention to provide a process for the recovery of 3-methylbut-3-en-1-ol, of isobutene and of the solvents from the reaction mixture for the preparation of methylbut-3-en-1-ol, which is efficient and simple and allows essentially a reduced number of distillations and yet the recovery of three components of the reaction mixture i.e. 3-methylbut-3-en-1-ol, isobutene and optionally the solvents with high purity and in high amount. The process should economically advantageous and should especially allow reducing energy consumption and number of required stages.

The above problem is solved by the processes disclosed herein below, wherein 3-methylbut-3-en-1-ol, isobutene and the solvents are obtained in high purity and high amount by using a minimum number of distillation steps.

A. Process for Recovering methylbut-3-en-1-ol

Therefore, the present invention relates to a process for recovering 3-methylbut-3-en-1-ol from a feed stream F1 comprising 3-methylbut-3-en-1-ol, one or more solvents, water, and isobutene, the process comprising (i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;

(ii) subjecting the bottoms stream B1 (Su K1200) to distillation in a second distillation unit (K1300), obtaining a bottoms stream B2 (Su K1300) comprising 3-methylbut-3-en-1-ol and a top stream T2 (De K1300) comprising water;

(iii) subjecting the bottoms stream B2 to distillation in a third distillation unit (K1500), obtaining a top stream T3 (De K1500) comprising 3-methylbut-3-en-1-ol and a bottoms stream B3 (Su K1500);

wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol relative to the bottoms stream B1, wherein the top stream T3 (De K1500) is enriched in methylbut-3-en-1-ol relative to the bottoms stream B2 (Su K1300).

The term "enriched" in the present context when referred to a component of a stream means that the weight percentage of a component in a stream B is higher than the weight percentage of this component in the stream A from which said stream B is originated. In terms of absolute weight value the amount of this component maybe the same in the two streams. However the weight percentage of said component in the enriched stream B is higher than in the original stream A. For example the amount of methylbut-3-en-1-ol in the feed stream F1 and in the bottoms stream B1 can be the same and the weight percentage of methylbut-3-en-1-ol in F1 can be 13.8 weight-% and in the bottoms stream B1 can be of 21.6 weigh-%. B1 hence is enriched in methylbut-3-en-1-ol. The absolute amount in both streams remains the same as all the methylbut-3-en-1-ol of the feed stream F1 is recovered in the bottoms stream B1. The term "depleted" in the present context when referred to a component of a stream means that the weight percentage of this component in a stream B is lower than the weight percentage of this component in the stream A from which said stream B is originated. As explained above, in terms of absolute weight value the amount of this component maybe the same in the two streams. However the weight-percentage of said component in the depleted stream is lower than in the original stream.

Feed Stream (F1)

Generally, there is no specific restriction with respect to the feed stream F1 as far as it comprises 3-methylbut-3-en-1-ol, the one or more solvents, water, and isobutene. The feed stream F1 is generally the product stream of a process for preparing 3-methylbut-3-en-1-ol.

Preferably, the feed stream F1 (feed_K1200) is a reaction mixture obtainable or obtained by a process for preparing 3-methylbut-3-en-1-ol, the process comprising (t) providing a mixture comprising formaldehyde, isobutene and the one or more solvents;

(tt) contacting the mixture provided in (t) with a condensation catalyst comprising, preferably consisting of an heterogeneous catalyst and obtaining the feed stream F1.

Heterogeneous catalyst in the present context is a catalyst for heterogeneous catalysis. The heterogeneous catalyst comprises, preferably consists of, a Lewis acid catalyst and/or a Brönsted acid catalyst, more preferably a Lewis acid catalyst wherein preferably the Lewis acid catalyst is a zeolitic material, a mesoporous silica, a metal oxide or mixed metal oxides supported rare earth metals and combination of two or more thereof. With regard to the zeolitic material, the zeolitic material is one or more of a zeolitic material comprising Si, 0, optionally Al, and a tetravalent element Y which is one or more of Sn, Ti and Zr, wherein in the framework structure of the zeolitic material the molar Al:Si ratio is in the range of from 0:1 to 0.001:1, a metal doped zeolite, preferably a rare-earth metal doped zeolite or a alkaline earth modified Al-containing zeolite.

The conversion of isobutene to isobutenol in particular via Prins reaction usually requires high pressures and high temperatures. The process becomes economically attractive only when it is carried out under mild conditions and with high conversion and selectivity. The condensation reaction according to (tt) can be carried out at mild conditions of temperature and pressure. Further if can be carried out using aqueous formaldehyde as aldehyde source which, in contrast to paraformaldehyde or other formaldehyde sources, has by far the highest relevance for an industrial-scale process. Further the 3-methylbut-3-en-1-ol can be easily separated Hence, the process for preparing the feed stream F1 prior to (i) comprises (t) providing a mixture comprising formaldehyde, isobutene and the one or more solvents;

(tt) contacting the mixture provided in (t) with a condensation catalyst comprising, preferably consisting of an heterogeneous catalyst and obtaining the feed stream F1.

Preferably, the feed stream F1 (feed_K1200) is a reaction mixture obtainable or obtained by a process for preparing 3-methylbut-3-en-1-ol, the process comprising (t) providing a mixture comprising formaldehyde, isobutene and the one or more solvents;

(tt) contacting the mixture provided in (t) with a condensation catalyst comprising a zeolitic material, obtaining the feed stream F1;

wherein the framework structure of the zeolitic material in (tt) comprises Si, 0, optionally Al, and a tetravalent element Y which is one or more of Sn, Ti and Zr, wherein in the framework structure of the zeolitic material in (tt), the molar Al:Si ratio is in the range of from 0:1 to 0.001:1.

Generally, there is no specific restriction with respect to the zeolitic material according to (tt) as far as the above features are fulfilled and provided that 3-methylbut-3-en-1-ol is obtained.

Preferably, the zeolitic material according to (tt) comprises, preferably consists of, a 10 membered-ring pores, or 12 membered-ring pores, or 10 membered-ring pores and 12 membered-ring pores. Preferably, the framework structure of the zeolitic material according to (tt) comprises, preferably has, the framework type BEA, MFI, MWW, MEL, MEL/MFI, GME, MOR, MTT, MTW, FER, or CON or a mixed structure thereof, or a mixture of these structures. More preferably, the framework structure of the zeolitic material according to (tt) comprises, preferably has, the framework type BEA, or MFI, or MWW or a mixed structure thereof, or a mixture of these structures. More preferably, the framework structure of the zeolitic material according to (tt) comprises, preferably has, the framework type BEA.

As disclosed above, the framework structure of the zeolitic material according to (tt) comprises Si, O and H and optionally Al. In addition, the framework structure of the zeolitic material according to (tt) has a molar Al:Si ratio, calculated as elemental Al and Si, in the range of from 0:1 to 0.001:1. Preferably, the framework structure of the zeolitic material in (tt) has a molar Al:Si ratio in the range of from 0:1 to 0.0001:1, more preferably in the range of from 0:1 to 0.00001:1, more preferably in the range of from 0:1 to 0.000001:1. More preferably, the framework structure of the zeolitic material in (tt) is free of aluminum. The term "free of aluminum" as used in this context means that aluminium is present in the zeolitic material, if at all, only in traces, i.e. in the form of unavoidable impurity.

The framework structure of the zeolitic material according to (tt), in addition to Si, 0, H and optionally Al, comprises a tetravalent element Y which is one or more of Sn, Ti and Zr. It is preferred that at least 99 weight-%, more preferably at least 99.5 weight-%, more preferably at least 99.9 weight-% of the framework structure of the zeolitic material according to (tt) consist of Si, Y, O and H, For example, at least 99.95 weight-% or at least 99.99 weight-% of the framework structure of the zeolitic material according to (tt) consist of Si, Y, O and H.

Generally, there is no specific restriction with respect to the amount of the tetravalent element Y in the framework structure of the zeolitic material according to (tt) provided that the catalytic activity is maintained. Preferably, the amount of the tetravalent element Y in the framework structure of the zeolitic material according to (tt) is in the range of from 0.5 to 20 weight-%, more preferably in the range of from 1 to 18 weight-%, more preferably in the range of from 1.5 to 17 weight-%, more preferably in the range of from 4 to 16 weight-%, based on the total weight of the zeolitic material.

It is further preferable that the framework structure does not comprise a trivalent element X which is B, more preferably does not comprise a trivalent element X which is one or more of B, In, Ga, and Fe, more preferably does not comprise a trivalent element X, other than optionally Al. In the context of the present invention, the term "no element X other than optionally Al" is to be understood in that the amount of the trivalent element X is in the range of from 0 to 1 weight-%, preferably in the range of from 0 to 0.1 weight-%, more preferably in the range of from 0 to 0.01 weight-%. The term "no element X" as used in this context means that the element X is present in the zeolitic material, if at all, only in traces, i.e. in the form of unavoidable Zeolitic materials, in the context of the present application, are naturally occurring or synthetically produced microporous crystalline materials having a three-dimensional framework structure formed from corner-linked tetrahedra. Preferably, the zeolitic material according to (tt) has acid sites comprising Brönsted and/or Lewis acid sites. Accordingly, the zeolitic material according to (tt) preferably has one desorption maximum in its desorption spectrum obtained by temperature-programmed desorption with $NH_3$ ($NH_3$-TPD) as described in Reference Example 1.4 herein. Preferably, the zeolitic material according to (tt) has a desorption maximum within the temperature ranges of from 0 to 250° C., in a temperature-programmed desorption with $NH_3$. The zeolitic material of the invention more preferably do not have ammonia desorption above 250° C., in a temperature-programmed desorption with $NH_3$.

The zeolitic material of framework type BEA is the more preferred. The zeolitic material of framework type BEA preferably comprises Y, more preferably comprises Sn, in an amount in the range of from 1 to 20 weight-%, more preferably in the range of from 2 to 18 weight-%, more preferably in the range of from 3 to 17 weight-%, more preferably in the range of from 4 to 16 weight-%, based on the total weight of the zeolitic material. Preferably, the framework structure of framework type BEA, apart from Sn, does not comprise any further tetravalent element Y.

Preferred zeolitic materials having framework type BEA and comprising Sn are disclosed in WO 2015/067654 A. These materials are preferably prepared by deboronation of a boron-containing zeolitic material having framework type BEA, followed by introducing the tin into the deboronated material and by an acid treatment, wherein the acid treatment is carried out with an aqueous solution having a pH of at most 5.

Thus, a zeolitic material having framework type BEA comprising Sn can be prepared by a process comprising
(1) providing a zeolitic material having a BEA framework structure comprising Si and O and Y wherein Y is the tetravalent element Sn, said BEA framework structure having vacant tetrahedral framework sites;
(2) providing a tin-ion source in solid form;
(3) incorporating tin into the zeolitic material provided in (1) by bringing the zeolitic material provided in (1) in contact with the tin-ion source provided in (2) under solid-state ion exchange conditions, obtaining a tin-containing zeolitic material having a BEA framework structure;
(4) subjecting the zeolitic material obtained from (3) to a heat treatment;
(5) treating the heat-treated zeolitic material obtained from (4) with an aqueous solution having a pH of at most 5.

The zeolitic material of (1) can for example be a deboronated zeolitic material having a BEA framework. The preparation of a deboronated zeolitic material having framework type BEA is disclosed in Reference Examples 5 and 6 of WO 2015/067654. The preparation of the tin-containing zeolitic material having a BEA framework is for example disclosed in Comparative Examples 1 to 4 of WO 2015/067654 A, and the acid treatment of the tin-containing zeolitic material having a BEA framework is disclosed in Examples 1 to 4 of WO 2015/067654 A.

As to the process conditions, generally there is no particular restriction provided that 3 methylbut-3-en-1-ol is obtained. For example, the contacting the mixture provided in (t) with the condensation catalyst according to (tt) can carried out in a batch mode or in a semi-continuous mode or in a continuous mode, although preferably the contacting is carried out in a continuous mode. Preferably, the mixture provided in (t) is contacted with the condensation catalyst according to (tt) in liquid phase and in liquid form. Preferably prior to (tt), the mixture provided in (t) is brought to a temperature in the range from 50 to 150° C., preferably in the range of from 80 to 120° C., more preferably in the range of from 95 to 110° C. Thereafter, the contacting in (tt) is carried out at a temperature of the mixture brought in contact with the condensation catalyst in the range of from 60 to 150° C., preferably in the range of from 70 to 115° C., more preferably in the range of from 75 to 105° C. As to the pressure of the contacting of (tt) there is no particular restriction. Generally, the contacting in (tt) is carried out at a pressure of the mixture brought in contact with the condensation catalyst in the range of from 0.01 to 40 bar(abs), preferably from 0.01 to 25 bar(abs), more preferably in the range of from 0.05 to 20 bar(abs). As to the weight hourly space velocity of the contacting of (tt) there is no particular restriction. Generally, the contacting in (tt) is carried out at a weight hourly space velocity in the range of from 0.1 to 1.0 $h^{-1}$; preferably the contacting of (t) is carried out at a weight hourly space velocity in the range of from 0.15 to 0.6 $h^{-1}$. The weight hourly space velocity is defined herein a as the mass flow rate of the formaldehyde, calculated as $CH_2O$ comprised in the mixture provided in (t) in kg/h divided by the mass of the zeolitic material comprised in the condensation catalyst in kg with which the mixture provided in (t) is contacted in (tt).

Hence, the process for preparing the feed stream F1 prior to (i) comprises
(t) providing a mixture comprising formaldehyde isobutene and the one or more solvents;
(tt) contacting the mixture provided in (t) with a condensation catalyst comprising a zeolitic material, obtaining the feed stream F1;
wherein the zeolitic material is as defined herein above.

With regard to mesoporous silica: mesoporous silica are known in the art: examples of mesoporous silica are MCM-41 and SBA-15. The mesoporous silica preferably comprises a metal such as Sn, Zr, Ti. Preferably the mesoporous silica is Sn-Mesoporous silica.

With regard to the metal oxide mixture, the metal oxide mixture comprise, preferably consists, of two or more of silica, alumina, TiO2, ZnO, ZrO2.

With regard to the supported rare earth metals they rare earth metals supported on a suitable support. Preferably the rare-earth metal is one or more of Ce, Y, La, Preferably the support is one or more of alumina, silica and a polymeric support.

Generally there is no restriction with respect to the composition of the feed stream F1, provided that it comprises 3-methylbut-3-en-1-ol, the one or more solvents, water, and isobutene. Preferably at least 5 weight-%, more preferably from 10 to 20 weight-% of the feed stream F1 (feed_K1200) consist of methylbut-3-en-1-ol, preferably at least 30 weight-%, more preferably from 40 to 50 weight-% of the feed stream F1 consist of the one or more solvents, preferably at least 20 weight-%, more preferably from 20 to 40 weight-% of the feed stream F1 consist of isobutene and preferably at least 1 weight-%, more preferably from 3 to 7 weight-% of the feed stream F1 consist of water, in each case based on the total weight of the feed stream F1. It is further conceived that at least 96 weight-%, preferably from 97 to 99 weight-% of the feed stream F1 consist of 3-methylbut-3-en-1-ol, the one or more solvents, water and isobutene, in each case based on the total weight of the feed stream F1.

It is conceivable that in addition to 3-methylbut-3-en-1-ol other compounds are formed during the process for preparing 3-methylbut-3-en-1-ol. The feed stream F1 may hence further comprise these compounds. For example, the feed stream F1 may further comprise one or more of 3-methylbutane-1,3-diol and the ester of formic acid and 3-methylbut-3-en-1-ol. It is conceived that these products, if formed, are present in small amounts in the feed stream F1. It is conceived that these compounds are undesirable product of the condensation reaction. Therefore preferably, at most 4 weight-%, more preferably at most 1 weight-% of the feed stream F1 consist of one or more of 3-methylbutane-1,3-diol and the ester of formic acid and 3-methylbut-3-en-1-ol.

Generally there is no limitation as to the temperature of the feed stream F1 to be fed into the distillation of (i). Preferably, the feed stream F1 (feed_K1200) subjected to distillation according to (i) is fed into the distillation unit at temperature in the range of from 40 to 160° C., more preferably in the range of from 90 to 110° C.

Distillation Step (i)

The process as disclosed above comprises (i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene.

The purpose of the distillation of (i) is to remove isobutene from the feed stream F1. Hence, according to (i) isobutene is separated from methylbut-3-en-1-ol, the one or more solvents and water by distillation, by subjecting the feed stream F1 to distillation conditions in a first distillation unit and by obtaining a bottoms stream B1 which is enriched in methylbut-3-en-1-ol, in the one or more solvents and in water and is depleted in isobutene—all compared to the feed stream F1 subjected to distillation conditions- and a top stream T1 which is enriched in isobutene compared to the feed stream F1 subjected to distillation conditions. As it is disclosed herein below in details the distillation conditions of (i) vary according to the one or more solvents comprised in the feed stream F1. In general two aspects can be envisaged according to the one or more solvents comprised in the feed stream F1, the first aspects wherein the one or more solvents have a boiling point higher than the boiling point of methylbut-3-en-1-ol, the second wherein the one or more solvents have a boiling point lower than the boiling point of methylbut-3-en-1-ol, wherein the boiling point of 3-methylbut-3-en-1-ol is in the range of from 130 to 132° C. at an absolute pressure of 1 bar.

Bottoms Stream B1

In the distillation step (i) a bottoms stream is formed. Generally, there is no specific restriction with respect to the composition of the bottoms stream B1, provided that it comprises methylbut-3-en-1-ol, the one or more solvents and water and is enriched in methylbut-3-en-1-ol, the one or more solvents and water and is depleted in isobutene compared to the feed stream F1 subjected to distillation conditions. Preferably at least 10 weight-%, more preferably from 15 to 30 weight-% of the bottoms stream B1 (Su K1200) consist of methylbut-3-en-1-ol, preferably at least 50 weight-%, more preferably from 60 to 80 weight-% of the bottoms stream B1 (Su K1200) consist in the one or more solvents, preferably at least 3 weight-%, more preferably from 5 to 9 weight-% of the bottoms stream B1 (Su K1200) consist of water and preferably less than 0.1 weight-%, more preferably from 0.01 to 0.09 weight-% of the bottoms stream B1 consist of isobutene. It conceived that at least 96 weight-%, preferably from 97 to 99 weight-% of the bottoms stream B1 consist of 3-methylbut-3-en-1-ol, the one or more sol- vents and water, in each case based on the total weight of the bottoms stream B1.

Preferably the bottoms stream B1 is liquid.

A.1 Process Wherein the One or More Solvents have a Boiling Point Higher than the Boiling Point of Methylbut-3-En-1-Ol Distillation Step (i) (K1200): Distillation of the Feed Stream F1

The process as disclosed above comprises (i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene.

As mentioned above the distillation of (i) has the purpose to separate 3-methylbut-3-en-1-ol from isobutene. In the distillation step (i) a bottoms stream B1 enriched in 3-methylbut-3-en-1-ol, the one or more solvents and water and a top stream T1 enriched in isobutene compared to the feed stream F1 subjected to distillation conditions are recovered.

According to (i), methylbut-3-en-1-ol, the one or more solvents and water are separated from the feed stream F1 by distillation, comprising subjecting the feed stream F1 to distillation conditions in a first distillation unit, preferably a distillation tower. From the from the distillation tower, a bottoms stream B1 enriched in methylbut-3-en-1-ol, the one or more solvents and water and a top stream T1 enriched in isobutene are obtained. Preferably B1 is obtained as liquid bottoms stream and T1 is obtained as gaseous top stream.

As to the distillation conditions, generally there is no particular restriction provided that a bottoms stream B1 and a top stream T1 as disclosed herein are obtained. Preferably, this distillation tower has from 5 to 40, more preferably from 15 to 25 theoretical plates. The distillation tower is preferably operated at a top pressure in the range of from 4 to 15 bar(abs), more preferably in the range of from 7 to 13 bar(abs). The distillation tower is preferably operated at a temperature at the bottom of the tower in the range of from 140 to 190° C., more preferably in the range of from 170 to 180° C. and at a temperature at the top of the tower in the range of from 40 to 80° C., more preferably in the range of from 60 to 75° C.

Feed Stream F1

The feed stream F1 is as disclosed herein above. With regard to the one or more solvents comprised in the feed stream F1, generally, there is no specific restriction provided that they are suitable for the conversion of isobutene into 3-methylbut-3-en-1-ol in the presence of formaldehyde the condensation catalyst disclosed herein above preferably carried out with a zeolitic material as disclosed herein above and provided that the one or more solvents have a boiling point higher than the boiling point of 3-methylbut-3-en-1-ol wherein the boiling point of 3-methylbut-3-en-1-ol, wherein the boiling point of 3-methylbut-3-en-1-ol is in the range of from 130 to 132° C. at an absolute pressure of 1 bar. Preferably the one or more solvents have a boiling point in the range of from 140 to 240° C. at an absolute pressure of 1 bar, more preferably in the range of from 160 to 200° C. at an absolute pressure of 1 bar.

It is further preferred that the one or more solvents is one or more of a mono-hydroxy alcohol, a poly-hydroxy alcohol and a ketone. According to a further preferred embodiment, the mono-hydroxy alcohol is a secondary or tertiary alcohol. Preferably, the secondary and tertiary alcohols are one or more of 1-pentanol (138° C.), 2-hexanol (140° C.), 2-methyl-hexanol (142° C.), 4-methyl-hexanol (151° C.), 3-methyl-hexanol (152° C.), 3-ethylhexanol (159° C.), 4-heptanol (154° C.), 2-methyl-2-heptanol (157° C.), 3-heptanol (157° C.), 2-heptanol (158° C.), 3-ethyl-3-hexanol (159° C.), 3-methyl-2-heptanol (166° C.), 2-methyl-4-heptanol (166° C.), 4-ethyl-4-heptanol (179° C.), 2-octanol (180° C.), ethylhexanol (185° C.). According to a further preferred embodiment, the polyhydroxy alcohol is one or more of propanediol (187° C.), glycol (198° C.) and 1,4-butanediol (229° C.). According to a further preferred embodiment the ketone is one or more of cyclo-2-penten-1-on (153° C.), cyclohexanone (156° C.) and cycloheptanone (180° C.). More preferably, the one or more solvents is 2-ethylhexanol. The boiling points in parenthesis are at an absolute pressure of 1 bar. They are indicative values to show that the solvent mentioned meets the requirement of having a boiling point higher than the boiling point of 3-methylbut-3-en-1-ol. They are not meant to limit the scope of the present invention.

The feed stream F1 may additionally comprise solvents having a boiling point lower than the boiling point of 3-methylbut-3-en-1-ol. It is conceived that at most the 0.6 weight-% of the feed stream F1, preferably at most 0.4 weight-% of the feed stream F1 consists of these lower boiling point solvents, based on the total weight of the feed stream F1. More preferably, the feed stream F1 does not comprise solvents having a boiling point lower than the boiling point of 3-methylbut-3-en-1-ol. Examples of the lower boiling point solvents are methanol and tert-butanol. In the process as disclosed herein, it is conceived that these solvents are not recovered together with the one or more solvents having a boiling point higher than the boiling point of 3-methylbut-3-en-1-ol. Preferably these lower boiling point solvents are recovered in part in the top stream (De_K1400 in FIG. 1) of the fourth (K1400) distillation unit and in part with the recovery of isobutene via the top stream T2. The feed stream F1 may hence further comprise methanol. Preferably at most 0.9 weight-%, more preferably at most 0.4 weight-% of the feed stream F1 consist of methanol based on the total weight of the feed stream F1. The feed stream F1 may hence further comprise tert-butanol. Preferably at most 0.5 weight-%, more preferably at most 0.1 weight-% of the feed stream F1 consist of tert-butanol based on the total weight of the feed stream F1.

As disclosed above, it is conceivable that in addition to 3-methylbut-3-en-1-ol other compounds are formed during the process for preparing 3-methylbut-3-en-1-ol. The feed stream F1 may hence further comprise these compounds. For example, the feed stream F1 may further comprise one or more of 3-methylbutane-1,3-diol and the ester of formic acid and 3-methylbut-3-en-1-ol. It is conceived that these products, if formed, are present in small amounts in the feed stream F1. It is conceived that these compounds are undesirable product of the condensation reaction. Preferably at most 4 weight-%, more preferably at most 1 weight-% of the feed stream F1 consist of one or more of 3-methylbutane-1,3-diol and the ester of formic acid and 3-methylbut-3-en-1-ol.

Preferably at least 99 weight-%, more preferably at least 99.8 weight-% of the 3-methylbutane-1,3-diol comprised in the feed stream F1 is recovered in the top stream of the fifth (K1600) distillation unit. Preferably at least 99 weight-%, more preferably at least 99.8 weight-% of the ester of formic acid and 3-methylbut-3-en-1-ol comprised in the feed stream F1 is recovered in the bottoms stream B4 (De_K1400) of the fourth (K1400) distillation unit.

Bottoms Stream B1

The bottoms stream B1 is recovered from the bottoms of the first distillation unit. Generally, there is no specific restriction with respect to the composition of the bottoms stream B1, provided that B1 is enriched in methylbut-3-en-1-ol, the one or more solvents and water and is depleted in isobutene compared to the feed stream F1 subjected to distillation conditions. Preferably at least 10 weight-%, more preferably from 15 to 30 weight-% of the bottoms stream B1 (Su K1200) consist of methylbut-3-en-1-ol, preferably at least 50 weight-%, more preferably from 60 to 80 weight-% of the bottoms stream B1 (Su K1200) consist in the one or more solvents, preferably at least 3 weight-%, more preferably from 5 to 9 weight-% of the bottoms stream B1 (Su K1200) consist of water and preferably less than 0.1 weight-%, more preferably from 0.01 to 0.1 weight-% of the bottoms stream B1 consist of isobutene, in each case based on the total weight of the bottoms stream B1. It conceived that at least 96 weight-%, preferably from 97 to 99 weight-% of the bottoms stream B1 consist of 3-methylbut-3-en-1-ol, the one or more solvents and water, in each case based on the total weight of the bottoms stream B1.

It is conceivable that in addition to 3-methylbut-3-en-1-ol, the one or more solvents and water, the bottoms stream B1 optionally comprises other compounds that were comprised in the feed stream F1. For example, the bottoms stream B1 may further comprise one or more of 3-methylbutane-1,3-diol and the ester of formic acid and 3-methylbut-3-en-1-ol. It is conceived that these products, if present, are present in small amounts in the bottoms stream B1. Preferably at most 2 weight-%, more preferably at most 1.5 weight-% of the bottoms stream B1 consist of 3-methylbutane-1,3-diol. Preferably at most 1 weight-%, more preferably at most 0.5 weight-% of the bottoms stream B1 consist of the ester of formic acid and 3-methylbut-3-en-1-ol. The percentage values are based on the total weight of the bottoms stream B1.

With regard to the one or more solvents of the bottoms stream B1, the one or more solvents have a boiling point higher than the boiling point of 3-methylbut-3-en-1-ol, wherein the boiling point of 3-methylbut-3-en-1-ol is in the range of from 130 to 132° C. at an absolute pressure of 1 bar and are as disclosed herein above.

It is further conceivable that the bottoms stream B1 comprises one or more solvents having a boiling point lower than 3-methylbut-3-en-1-ol, such as methanol and tert-butanol. It is conceived that less than 1 weight-%, preferably less than 0.5 weight-% of the bottoms stream B1 consist of these one or more solvents having a boiling point lower than 3-methylbut-3-en-1-ol. It is conceived that less than 0.5 weight-%, preferably less than 0.2 weight-% of the bottoms stream B1 consist of methanol. It is conceived that less than 0.5 weight-%, preferably less than 0.2 weight-% of the bottoms stream B1 consist of tert-butanol. All the percentage values are based on the total weight of the bottoms stream B1.

Preferably, the bottoms stream B1 is liquid.

Distillation Step (ii) (K1300): Distillation of the Bottoms Stream B1

The process as disclosed above comprises (ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water.

According to step (ii) the bottoms stream B1 (Su K1200) is subjected to distillation in a second distillation unit (K1300). A bottoms stream B2 (Su K1300) comprising 3-methylbut-3-en-1-ol and enriched in the one or more solvents and a top stream T2 (De K1300) comprising 3-methylbut-3-en-1-ol and enriched in water are obtained.

The purpose of step (ii) is to separate water from 3-methylbut-3-en-1-ol and the one or more solvents. The step efficiently separates water from the one or more solvents, however part of the 3-methylbut-3-en-1-ol is removed together with water and is recovered in the top stream T2. This portion of 3-methylbut-3-en-1-ol can be, preferably is, recovered and recycled into the second distillation unit to render more economically effective the process for recovering 3-methylbut-3-en-1-ol. The recovery from the top stream T2 and the recycling of 3-methylbut-3-en-1-ol in the second distillation unit is disclosed below in the paragraph "Recovery of 3-methylbut-3-en-1-ol from T2".

According to (ii), the one or more solvents and part of 3-methylbut-3-en-1-ol are separated from water by distillation, comprising subjecting the bottoms stream B1 to distillation conditions in a second distillation unit, preferably a distillation tower. From the distillation tower, a bottoms stream B2 comprising methylbut-3-en-1-ol and enriched in the one or more solvents and a top stream T2 comprising methylbut-3-en-1-ol and enriched in water compared to the bottoms stream B1 are obtained.

As to the distillation conditions, generally there is no particular restriction provided that a bottoms stream B2 and a top stream T2 as disclosed herein are obtained Preferably the bottoms stream B2 is obtained as liquid bottoms stream and the top stream T2 is obtained as liquid top stream. Preferably, this distillation tower has from 15 to 50, more preferably from 15 to 25 theoretical plates. The distillation tower is preferably operated at a top pressure in the range of from 0.1 to 2 bar(abs), more preferably in the range of from 0.5 to 1.5 bar(abs).

For solvents having a boiling point higher than the boiling point of methylbut-3-en-1-ol, the temperature of the top of the distillation tower is set such that an efficient separation of methylbut-3-en-1-ol from the one or more solvents is carried out. The distillation tower is for example operated at a temperature at the bottoms of the tower in the range of from 130 to 180° C., preferably in the range of from 150 to 160° C. and at a temperature at the top of the tower in the range of from 60 to 110° C., preferably in the range of from 85 to 95° C. For example a distillation tower having 35 theoretical plates is operated at a temperature of about 90° C. when the solvent is 2-ethyl-hexanol.

Bottoms Stream B2

Generally, there is no specific restriction with respect to the composition of the bottoms stream B2 obtained from (i), provided that it comprises methylbut-3-en-1-ol, is enriched in the one or more solvents and is depleted in water compared to the bottoms stream B1 subjected to distillation conditions. Preferably at least 10 weight-%, more preferably from 20 to 35 weight-% of the bottoms stream B2 (Su K1300) consist of methylbut-3-en-1-ol, preferably at least 55 weight-%, more preferably from 70 to 90 weight-% of the bottoms stream B2 (Su K1300) consist of the one or more solvents, and preferably less than 0.05 weight-%, more preferably from 0.002 to 0.005 weight-% of the bottoms stream B2 (Su K1300) consist of water. It is conceived that at least 96 weight-%, preferably from 98 to 99 weight-% of the bottoms stream B2 consist of 3-methylbut-3-en-1-ol and the one or more solvents. The percentage values are in each case based on the total weight of the bottoms stream B2.

Optionally the bottoms stream B2 comprises 3-methylbutane-1,3-diol. Preferably, less than 2 weight-%, more preferably less than 1.7 weight-% of the bottoms stream B2 consist of 3-methylbutane-1,3-diol. Optionally the bottoms stream B2 comprises the ester of formic acid and 3-methylbut-3-en-1-ol. Preferably, less than 100 weight-ppm, more preferably less than 60 ppm-weight of the bottoms stream B2 consist of the ester of formic acid and 3-methylbut-3-en-1-ol. The percentage values are in each case based on the total weight of the bottoms stream B2. Preferably, the bottoms stream B2 does not comprise the above mentioned one or more solvents having a boiling point lower than methylbut-3-en-1-ol.

Top Stream T2

The top stream T2 is recovered from the top of the second distillation unit. Generally, there is no specific restriction with respect to the composition of the top stream T2 provided that is enriched in water and is depleted of the one or more solvents compared to the bottoms stream B1 subjected to distillation conditions. Preferably at least 10 weight-%, more preferably from 20 to 35 weight-% of the top stream T2 (De K1300) consist of water. As mentioned above part of 3-methylbut-3-en-1-ol comprised in B1 is recovered in the top stream T2. Preferably, at least 40 weight-%, more preferably from 50 to 75 weight-% of the top stream T2 (De K1300) consist of 3-methylbut-3-en-1-ol, and preferably less than 0.05 weight-%, more preferably from 0.002 to 0.005 weight-% of the top stream T2 (De K1300) consist of the one or more solvents. It is conceived that at least 96 weight-%, preferably from 98 to 99 weight-% of the top stream T2 consist of 3-methylbut-3-en-1-ol and water. The percentage values are in each case based on the total weight of the top stream T2.

When the bottoms stream B1 comprises the ester of formic acid and 3-methylbut-3-en-1-ol, it is conceived that the top stream T2 comprises the ester of formic acid and 3-methylbut-3-en-1-ol. It is conceived that when the feed stream F1 comprises the ester of formic acid and 3-methylbut-3-en-1-ol at least 99 weight-%, preferably at least 99.8 weight-% of the ester of the formic acid and 3-methylbut-3-en-1-ol comprised in the feed stream F1 is eliminated via the top stream T2 and less than 1 weight-%, preferably less than 0.12 weight-% of the ester of the formic acid and 3-methylbut-3-en-1-ol comprised in the feed stream F1 is eliminated via the top stream T1 and the bottoms stream B2.

When the bottoms stream B1 comprises 3-methylbutane-1,3-diol, it is conceived that the top stream T2 preferably does not comprises 3-methylbutane-1,3-diol. It is conceived that when the feed stream F1 comprises 3-methylbutane-1,3-diol, 3-methylbutane-1,3-diol is eliminated via the bottoms stream B2.

When the bottoms stream B1 comprises one or more solvents having a boiling point lower than 3-methylbut-3-en-1-ol, such as methanol and tert-butanol it is conceived that the top stream T2 comprises said one or more solvents. It is conceived that when the feed stream F1 comprises said one or more solvents at least 40 weight-%, preferably at least 50 weight-% of said one or more solvents comprised in the feed stream F1 is eliminated via the top stream T2 and/or via the top stream T4 (De_K1400) of the forth distillation unit as disclosed herein below in the paragraph "Recovery of 3-methylbut-3-en-1-ol (B 1310, W1420 and B 1420) from T2".

It is conceived that when the bottoms stream B1 comprises methanol, the top stream T2 comprises methanol. It is conceived that when the feed stream F1 comprises methanol at least 40 weight-%, preferably at least 50 weight-% of the methanol comprised in the feed stream F1 is eliminated via the top stream T2 and/or via the top stream T4 as disclosed herein below in the paragraph "Recovery of 3-methylbut-3-en-1-ol (B 1310, W1420 and B 1420) from T2.

It is conceived that when the bottoms stream B1 comprises tert-butanol the top stream T2 comprises tert-butanol.

It is conceived that when the feed stream F1 comprises tert-butanol at least 80 weight-%, preferably at least 85 weight-% of the tert-butanol comprised in the feed stream F1 is eliminated via the top stream T2 and/or via the top stream T4 as disclosed herein below "Recovery of 3-methylbut-3-en-1-ol (B 1310, W1420 and B 1420) from T2".

Reflux of a Portion of the Top Stream T2 (Portion PT2)

In order to increase the efficiency of the second distillation it is further contemplated to reflux part of the top stream T2 into the second distillation unit.

Hence, it is contemplated separating a portion PT2 (Reflux_K1300) of the top stream T2 from T2 and feeding the portion PT2 back to the top of the second distillation unit according to (ii). The portion PT2 is preferably in the range of from 60 to 95 weight-%, more preferably from 80 to 90 weight-% of the top stream T2, based on the total weight of the top stream T2. The temperature of the portion PT2 is preferably in the range of from 20 to 60° C., more preferably in the range of 35 to 45° C. The portion PT2 is returned to the top of second distillation unit as reflux stream. Inside the column the downflowing reflux liquid provides cooling and condensation of the upflowing vapors thereby increasing the efficiency of the separation of the one or more solvents and 3-methylbut-3-en-1-ol from water.

Vapor-Liquid Separation of the Bottoms Stream B1 (B1300_Flash) Prior to (ii)

To render more efficient the separation process it is further contemplated that the bottoms stream B1 after (i) and prior to (ii) is preferably subjected to a vapor-liquid separation (B1300_Flash) in a phase separation unit. A liquid stream L7 (B1300_Fl) and a gas stream G7; (B1300_Gas) are obtained from the vapor-liquid separation step. Preferably the liquid stream L7 is enriched in the one or more solvents with respect to the bottoms stream B1 subjected to vapor-liquid separation conditions. Preferably the gas stream G7 is enriched in water with respect to the bottoms stream B1 subjected to vapor-liquid separation conditions. The gas stream G7 and the liquid stream L7 are then subjected to distillation according to (ii). Generally, the gas stream G7 and the liquid stream L7 are fed at the side of the distillation unit, preferably are fed above theoretical plate 20.

Generally there is no restriction as to the conditions of the vapor-liquid separation provided that the gas stream G7 is enriched in water with respect to the bottoms stream B1 subjected to vapor-liquid separation conditions and the liquid stream L7 is enriched in the one or more solvents with respect to the bottoms stream B1 subjected to vapor-liquid separation conditions. The gas stream G7 and the liquid stream L7 are then subjected to distillation according to (ii). Preferably, the vapor-liquid separation (B1300_Flash) is carried out at a temperature in the range of from 90 to 140° C., more preferably in the range of from 100 to 130° C. Preferably the vapor-liquid separation (B1300_Flash) is carried out at a pressure in the range of from 0.1 to 2 bar(abs), more preferably in the range of from 0.5 to 1.5 bar(abs).

Distillation Step (Hi) (K1500): Distillation of the Bottoms Stream B2

The process as disclosed above further comprises:
(iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising the one or more solvents.

The purpose of the distillation step (iii) is to separate 3-methylbut-3-en-1-ol from the one or more solvents comprised in the bottoms stream B2. The step efficiently separates 3-methylbut-3-en-1-ol from the one or more solvents.

According to step (Hi) the bottoms stream B2 (Su K1300) is subjected to distillation in a third distillation unit (K1500), a top stream T3 (De K1500) enriched in 3-methylbut-3-en-1-ol and a bottoms stream B3 (Su K1500) enriched in the one or more solvents are obtained.

According to (iii), 3-methylbut-3-en-1-ol is separated from the one or more solvents by distillation, comprising subjecting the bottoms stream B2 to distillation conditions in a third distillation unit, preferably a distillation tower. From the distillation tower, a top stream T3 enriched in methylbut-3-en-1-ol compared to the bottoms stream B2 subjected to distillation conditions and a bottoms stream B3 enriched in the one or more solvents compared to the bottoms stream B2 subjected to distillation conditions are obtained. Preferably the bottoms stream B3 is obtained as liquid bottoms stream and the top stream T3 is obtained as liquid top stream.

As to the distillation conditions, generally there is no particular restriction provided that a bottoms stream B3 and a top stream T3 as disclosed herein are obtained. Preferably, this distillation tower has from 10 to 45, more preferably from 20 to 30 theoretical plates. The distillation tower is preferably operated at a top pressure in the range of from 0.03 to 1.5 bar(abs), more preferably in the range of from 0.09 to 0.5 bar(abs). The distillation tower is preferably operated at a temperature at the bottoms of the tower in the range of from 90 to 150° C., more preferably in the range of from 120 to 140° C. and preferably at a temperature at the top of the tower in the range of from 45 to 90° C., more preferably in the range of from 65 to 75° C.

Top Stream T3 (De K1500)

The top stream T3 is recovered from the top of the third distillation unit. Generally, there is no specific restriction with respect to the composition of the bottoms stream T3, provided that it comprises methylbut-3-en-1-ol. Preferably, at least 97 weight-%, more preferably from 99.5 to 99.95 weight-%, more preferably from 99.8 to 99.9 weight-% of the top stream T3 (De K1500) consist of 3-methylbut-3-en-1-ol, based on the total weight of the top stream T3 (De K1500). The one or more solvents, the ester of formic acid and 3-methylbut-3-en-1-ol may be found in an amount lower than 200 weight-ppm, preferably lower than 100 weight-ppm of the top stream T3. The percentage values in each case are based on the total weight of the top stream T3.

The process according to the invention is highly effective in the recovery of methylbut-3-en-1-ol. According to the process disclosed above, 3-methylbut-3-en-1-ol is recovered in high purity and high percentage. Preferably at least 97 weight-%, more preferably at least 99.5 weight-% of the 3-methylbut-3-en-1-ol comprised in the feed stream F1 are recovered via T3.

Vapor-Liquid Separation of the Bottoms Stream B2 (B1500) Prior to (iii)

To render more efficient the separation process it is contemplated that the bottoms stream B2 after (ii) and prior to (iii) is preferably subjected to a vapor-liquid separation (B1500) in a phase separation unit. A liquid stream L8 (B1500_Fl) and a gas stream G8 (B1500_Br) are obtained. Both streams comprise 3-methylbut-3-en-1-ol and the one or more solvents. L8 is richer in the one or more solvents than the gas stream G8 and the gas stream G8 is richer in 3-methylbut-3-en-1-ol than the liquid stream L8. The gas stream G8 and the liquid stream L8 are then subjected to distillation according to (iii). Generally, the gas stream G8 and the liquid stream L8 are fed at the side of the third distillation unit, preferably the gas stream G8 and the liquid stream L8 are fed above the theoretical plate 15.

Generally there is no restriction as to the conditions of the vapor-liquid separation provided that the liquid stream L8 and the gas stream G8 as disclosed herein above are obtained. Preferably, the vapor-liquid separation (B1500) is carried out at a temperature in the range of from 70 to 140° C., more preferably in the range of from 90 to 105° C. Preferably the vapor-liquid separation (B1500) is carried out at a pressure in the range of from 0.005 to 0.8 bar(abs), more preferably in the range of from 0.08 to 0.2 bar(abs).

Step (iv): Recovery of 3-Methylbut-3-En-1-Ol (B 1310, W1420 and B 1420) from T2 and Recycling in (ii)

As mentioned above, the top stream T2 comprises, in addition to water, 3-methylbut-3-en-1-ol. The present invention relates to a process as disclosed herein wherein the 3-methylbut-3-en-1-ol comprised in the top stream T2 is recycled in the second distillation unit and recovered in the top stream T3. By means of this additional step the process for recovering the 3-methylbut-3-en-1-ol from the feed stream F1 is highly efficient and at least 97 weight-%, preferably at least 99.5 weight-% of the 3-methylbut-3-en-1-ol comprised in the feed stream F1 are recovered via the top stream T3. The process is hence economically advantageous as no lost or almost no lost of the valuable product 3-methylbut-3-en-1-ol occurs. Further, the purpose of step (iv) is to separate 3-methylbut-3-en-1-ol from other compounds such as the ester of formic acid and 3-methylbut-3-en-1-ol and the one or more solvents having a boiling point lower than the boiling point of 3-methylbut-3-en-1-ol such as methanol, tert-butanol that can be present in the feed stream F1 and in the top stream T2.

It is further conceived isobutene may be present in the top stream T2. In this case less than 0.2 weight-%, preferably less than 0.1 weight-% of the isobutene comprised in the feed stream F1 is comprised in in the top stream T2. In the case, the purpose of step (iv) is additionally to separate 3-methylbut-3-en-1-ol from the residual isobutene that has not been separated via the top stream T1.

Hence the process as disclosed above preferably further comprises (iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq.

According to (iv), 3-methylbut-3-en-1-ol is partially separated from water by phase separation. To render more efficient the above process it is contemplated that the top stream T2 after (ii) is subjected to a phase separation (B1310) (iv) in a phase separation unit. An aqueous liquid stream L2aq (B 1310 WP) comprising water and 3-methylbut-3-en-1-ol and an organic liquid stream L2or (B1310 OP) comprising 3-methylbut-3-en-1-ol and water are obtained whereon the organic liquid stream L2or is enriched in 3-methylbut-3-en-1-ol relative to the top stream T2 (De K1300). Preferably at least 96 weight-%, more preferably from 97 to 98.7 weight-% of the 3-methylbut-3-en-1-ol comprised in the top stream T2 is recovered in the organic liquid stream L2or. The organic liquid stream L2or is richer in 3-methylbut-3-en-1-ol than the aqueous liquid stream L2aq.

Generally there is no specific restriction with respect to the composition of the organic liquid stream L2or (B1310 OP) provided that a stream L2or as disclosed above is obtained. Preferably at least 50 weight-%, more preferably from 55 to 65 weight-% of the stream L2or consist of 3-methylbut-3-en-1-ol, preferably less than 15 weight-%, more preferably from 13 to 10 weight-% of the stream L2or consist of water. The percentage values in each case are based on the total weight of the stream L2or.

Optionally the stream L2or comprises the ester of formic acid and 3-methylbut-3-en-1-ol. Preferably, less than 30 weight-%, more preferably from 15 to 25 weight-% of stream L2or consist of the ester of formic acid and 3-methylbut-3-en-1-ol. The percentage values are in each case based on the total weight of the stream L2or. In case the top stream T2 comprises the ester of formic acid and 3-methylbut-3-en-1-ol then the organic liquid stream L2or is richer in the ester of formic acid and 3-methylbut-3-en-1-ol than the aqueous liquid stream L2aq.

Optionally the stream L2or comprises the ester of formic acid and 3-methylbut-3-en-1-ol comprises the low boiling solvents and isobutene that were recovered in the top stream T2.

The organic liquid stream L2or is in part refluxed into the second distillation unit. It is contemplated with this regard that a portion PT2 (Reflux_K1300) and a portion L2or' (OP_Out) of the organic liquid stream L2or (B1310 OP) are separated from the organic liquid stream L2or (B1310 OP). The stream PT2 is fed back to the top of the distillation tower according to (ii), wherein the stream PT2 is preferably in the range of from 94 to 98 weight-%, preferably in the range of from 96 to 97 weight-% of L2or based in the total weight of L2or. Advantageously, according to this embodiment, 3-methylbut-3-en-1-ol is recycled in the second distillation unit K1300 without the need of a further distillation step. Preferably at least the 94 weight-%, more preferably from 95 to 97.5 weight % of the 3-methylbut-3-en-1-ol comprised in the top stream T2 is recycled in the second distillation unit via the reflux of portion PT2.

Generally, there is no restriction as to the conditions of the phase separation (iv) provided that the organic liquid steam L2or and the aqueous liquid stream L2aq as disclosed above are obtained. Preferably, the phase separation (B1310) is carried out at a temperature in the range of from 20 to 60° C., more preferably in the range of from 35 to 45° C. Preferably the phase separation (B1310) is carried out at a pressure in the range of from 0.05 to 3 bar(abs), more preferably in the range of from 0.5 to 1.5 bar(abs).

Distillation Step (iv-a): Distillation of the Streams L2or' and L2aq

The forth distillation of (iv-a) has the purpose to further recover into the distillation step (ii) the residual 3-methylbut-3-en-1-ol comprised in the streams L2or' and L2aq obtained from (iv) by further separation of 3-methylbut-3-en-1-ol from water. When the feed stream F1 comprises one or more solvents having a boiling point lower than 3-methylbut-3-en-1-ol such as methanol and tert-butanol and/or the ester of formic acid and 3-methylbut-3-en-1-ol it is conceived that the streams L2or' and L2aq comprises the one or more solvents having a boiling point lower than 3-methylbut-3-en-1-ol such as methanol and tert-butanol and/or the ester of formic acid and 3-methylbut-3-en-1-ol the step (iv-a). In this case step (iv-a) has preferably the additional purpose of separating 3-methylbut-3-en-1-ol from the one or more solvents having a boiling point lower than 3-methylbut-3-en-1-ol such as methanol and tert-butanol, and from the ester of formic acid and 3-methylbut-3-en-1-ol comprised in L2aq and in L2or.

According to (iv-a), the residual 3-methylbut-3-en-1-ol comprised in the streams L2or' and L2aq is partially separated from water by distillation and is separated from the other compounds as mentioned above that may be present in the top stream T2, comprising subjecting comprised in the streams L2or' and L2aq to distillation conditions in a fourth distillation unit, preferably a distillation tower.

Hence, the process above preferably further comprises (iv-a) subjecting the streams L2or' and L2aq to distillation (K1400) in a fourth distillation unit, obtaining a side stream S2 (DSA) comprising 3-methylbut-3-en-1-ol and water, wherein the side stream S2 (DSA) is preferably fed back to the distillation according to (ii) (K1300).

From the distillation tower, a side stream S2 (DSA) comprising methylbut-3-en-1-ol and water a top stream T4 (De_K1400) and a bottoms stream B4 (Su_K1400) are recovered.

The side stream S2 comprises 3-methylbut-3-en-1-ol and water. Preferably, other compounds such as the ester of formic acid and 3-methylbut-3-en-1-ol, the low boiling solvents such as methanol and tert-butanol and isobutene that were originally comprised in the feed stream F1 are present in the side stream S2 in a small amount. Preferably, at least 30 weight-%, more preferably from 45 to 60 weight-% of the side stream S2 (DSA) consist of methylbut-3-en-1-ol, preferably less than 70 weight-%, more preferably from 40 to 55 weight-% of the side stream S2 (DSA) consist of water. It is conceived that at least 97 weight-%, preferably from 99 to 99.5 weight-% of the side stream S2 (DSA) consist of 3-methylbut-3-en-1-ol and water, in each case based on the total weight of the side stream S2 (DSA). Hence, preferably, less than the 1 weight-%, more preferably less than 0.5 weight-% of the side stream S2 consist of the ester of formic acid and 3-methylbut-3-en-1-ol. Preferably less than the 1000 weight-ppm, more preferably less than 500 ppm weight of the side stream S2 consist of the low boiling solvent such as methanol and tert-butanol. Preferably less than the 300 ppb-weight, more preferably less than 250 ppb weight of the side stream S2 consist of isobutene. The percentage values are in each case based on the total weight of the side stream S2. Preferably the side stream S2 is a gaseous stream.

As to the distillation conditions, generally there is no particular restriction provided that a side stream S2 as disclosed herein is obtained. Preferably, this distillation tower has from 7 to 40, more preferably 17 to 28 theoretical plates. The distillation tower is preferably operated at a top pressure in the range of from in the range of from 0.05 to 4 bar(abs), more preferably in the range of from 0.5 to 1.5 bar(abs). The distillation tower is preferably operated at a temperature at the bottoms of the tower in the range of from 60 to 140° C., more preferably in the range of from 90 to 110° C. and at a temperature at the top of the tower in the range of from 40 to 95° C., more preferably in the range of from 60 to 70° C. Preferably, the aqueous liquid stream L2aq and the organic liquid stream L2or' are fed at the side of the fourth distillation unit. Preferably they are fed above the theoretical plate 12.

The top stream T4 (De_K1400) comprises water and preferably one or more of the ester of formic acid and 3-methylbut-3-en-1-ol, one or more solvents having a boiling point lower than 3-methylbut-3-en-1-ol such as methanol and tert-butanol, that were originally comprised in the feed stream F1. It is further contemplated that the top stream T4 comprises a residual amount of isobutene that was not recovered via the top stream T1 and was comprised in the bottoms streams B1and then in the top stream T2. Preferably, at least 97 weight-% of the ester of formic acid and 3-methylbut-3-en-1-ol comprised in the feed stream F1, more preferably from 97.5 to 99 weight-% are discharged in the top stream T4. Preferably, less than 0.1 weight-% of isobutene comprised in the feed stream F1, more preferably from 0.09 to 0.05 weight-% of the isobutene comprised in the feed stream F1 are discharged via the top stream T4. Preferably, less than 3 weight-% of water comprised in the feed stream F1, more preferably from 2.5 to 1 weight-% of the water comprised in the feed stream F1 are discharged via the top stream T4. Preferably, at least 40 weight-% of the one or more solvents having a boiling point lower than methylbut-3-en-1-ol comprised in the feed stream F1, more preferably from 45 to 60 weight-% are discharged via the top stream T4.

The bottoms stream B4 (Su_K1400) comprises water. Preferably at least 99 weight-% of the bottoms stream B4 consist of water, more preferably from 99.5 to 99.9 of the bottoms stream B4 consist of water based on the total weight of the bottoms stream B4. It is conceived that at least 95 weight-%, preferably from 96 to 98 weight-% of the water comprised in the feed stream F1 is discharged via the bottoms stream B4.

Heat Exchange with Side Stream S2

To render even more efficient to process of recovering of 3-methylbut-3-en-1-ol from the top stream T2, after (iv-a), the process preferably comprises subjecting the side stream S2 (DSA) to heat exchange (W4120) in a heat exchange unit. A condensed stream C3 (Kond W1420) comprising 3-methylbut-3-en-1-ol and water and an off gas stream are recovered. The off gas stream comprising water, and optionally residual amounts of low boiling solvents, 3-methylbut-3-en-1-ol, the ester of formic acid and 3-methylbut-3-en-1-ol and the 3-methylbutane-1,3-diol is discharged as waste. The stream C3 (Kond W1420) is preferably further subjected to phase separation (B 1420) in a phase separation unit. From the separation, an organic liquid stream L3or (B 1420_OP) comprising 3-methylbut-3-en-1-ol and water is obtained, wherein preferably the organic liquid stream L3or (B 1420_OP) is recycled to distillation according to (ii) (K1300).

Generally, there is no restriction as to the conditions of the heat exchange, provided that a condensed stream C3 as disclosed above is obtained. Preferably, the heat exchange (W4120) is carried out at a temperature in the range of from 65 to 140° C., preferably in the range of from 90 to 105° C., and at a pressure in the range of from 0.05 to 3 bar(abs), preferably in the range of from 0.5 to 1.5 bar(abs).

Generally, there is no restriction as to the conditions of the phase separation. Preferably, the phase separation (B1420) is carried out at a temperature in the range of from 65 to 140° C., preferably in the range of from 90 to 105° C., and at a pressure in the range of from 0.05 to 3 bar(abs), preferably in the range of from 0.5 to 1.5 bar(abs).

Generally there is no restriction as to the composition of the organic liquid stream L3or (B 1420_OP) provided that is enriched in 3-methylbut-3-en-1-ol relative to the condensed stream C3 (Kond W1420). Preferably, at least 50 weight-%, preferably from 70 to 80 weight-% of the organic liquid stream L3or (B 1420_OP) consist of methylbut-3-en-1-ol, and less than 50 weight-%, preferably from 20 to 30 weight-% of the organic liquid stream L3or (B 1420_OP) consist of water, in each case based on the total weight of the organic liquid stream L3or (B 1420_OP). It is contemplated that the organic liquid stream L3or (B 1420_OP) additionally may comprises one or more of the ester of formic acid and 3-methylbut-3-en-1-ol, methanol, tert-butanol and isobutene. Preferably, less than 1.5 weight-% of L3or consist of the ester. Preferably, less than 200 ppb-weight of L3or consist of isobutene. Preferably, less than 700 weight-ppm of L3or consist of methanol. Preferably, less than 50 weight-ppm of L3or consist of tert-butanol.

The organic liquid stream L3or is recycled back to the second distillation unit, preferably at the side of the distillation unit, more preferably at the side of the distillation unit above the theoretical plate 17 at a temperature in the range of 136-138° C.

From the phase separation an aqueous liquid stream L3aq (B 1420_WP) is further obtained. Preferably the stream L3aq is recycled back to the fourth distillation unit.

Distillation step (v): High boiling solvents recovery (K1600)

The present invention further contemplates a process wherein the one or more solvents recovered from the bottoms stream B3 are recovered as highly pure solvents. The bottoms stream B3 in fact may comprise high boilers, for example 3-methylbutane-1,3-diol and middle boilers for example methylbut-3-en-1-ol and the ester of formic acid and 3-methylbut-3-en-1-ol that need to be removed from the one or more solvents to obtain a pure solvent Preferably these compounds are removed via distillation.

Bottoms Stream B3

The bottoms stream B3 (Su K1500) is recovered from the bottoms of the third distillation unit. As disclosed above the bottoms stream B3 is enriched in the one or more solvents relative to the bottoms stream B2 (Su K1300).

Generally, there is no specific restriction with respect to the composition of the bottoms stream B3, provided that it is enriched with the one or more solvents with respect to the bottoms stream B2. Preferably at least 95 weight-%, more preferably from 96 to 98 weight-% of the bottoms stream B3 (Su K1500) consist of the one or more solvents, (Su K1500), preferably less than 1000 weight-ppm, more preferably from 400 to 20 weight-ppm, more preferably from 200 to 50 weight-ppm of the bottoms stream B3 (Su K1500) consist of 3-methylbut-3-en-1-ol and preferably less than less than 100 weight-ppb, preferably from 50 to 0.1 weight-ppb of the bottoms stream B3 (Su K1500) consist of water, in each case based on the total weight of the bottoms stream B3. More preferably, the bottoms stream B3 does not comprise water. Preferably less than 2.5 weight-% of the bottoms stream B3, more preferably from 2.5 to 1.5 weight-%, more preferably from 2.3 to 1.8 weight-% of the bottoms stream B3 consist of 3-methylbutane-1,3-diol based on the total weight of the bottoms stream B3. It is conceived that at least the 99.5 weight-% of the one or more solvents comprised in the feed stream F1 are comprised in the bottoms stream B3, preferably from 99.6 to 99.9 weight-% of the one or more solvents comprised in the feed stream F1 are comprised in the bottoms stream B3. Hence the one or more solvents are efficiently recovered by means of the above disclosed process. It may be however further desirable to further purify the one of more solvents comprised in bottoms stream B3.

Distillation Step (v)

Therefore, the present invention relates to the process disclosed above wherein preferably the process further comprises recovering the one or more solvents comprised in the bottoms stream B3, (Su K1500) wherein the recovering preferably comprises (v) subjecting the bottoms stream B3 (Su K1500) to distillation (K1600) in a fifth distillation unit;
(vi) recovering a side stream S5 (Si K1600) from the fifth distillation unit, comprising the one or more solvents.

According to (v), the one or more solvents are separated from the high boilers such as 3-methylbutane-1,3-diol and the middle boilers such as methylbut-3-en-1-ol and the ester of formic acid and 3-methylbut-3-en-1-ol by distillation, comprising subjecting the bottoms stream B3 to distillation conditions in a fifth distillation unit, preferably a distillation tower. From the distillation tower, a side stream S5 (Si K1600) enriched in the one or more solvents compared to the bottoms stream B3 is obtained. Preferably the side stream S5 is obtained as liquid side stream.

As to the distillation conditions, generally there is no particular restriction provided that a side stream S5 as disclosed herein is obtained. Preferably, the distillation unit according to (v) comprises a distillation tower, more preferably a Petlyuk distillation tower comprising a pre-fractionator tower and a main tower, more preferably a dividing wall tower. Preferably the main distillation tower has from 10 to 45, more preferably from 20 to 30 theoretical plates. Preferably the distillation tower is a Petlyuk distillation wherein the distillation in the pre-fractionator tower is carried out at a pressure at the top of the tower in the range of from 0.005 to 1.5 bar(abs), preferably in the range of from 0.08 to 0.2 bar(abs) and a temperature at the bottoms of the tower in the range of from 100 to 135° C., preferably in the range of from 115 to 120° C., wherein the pre-fractionator tower has from 7 to 45, preferably from 17 to 25 theoretical plates. The distillation in the main tower is carried out at a pressure at the top of the main distillation tower in the range of from 0.004 to 2 bar(abs), preferably in the range of from 0.08 to 0.2 bar(abs) and a temperature at the bottoms of the main distillation tower in the range of from 115 to 175° C., preferably in the range of from 135 to 155° C., wherein the main distillation tower has from 12 to 75, preferably 30 to 40 theoretical plates.

Alternatively the distillation unit according to (v) is a dividing wall distillation tower, wherein preferably the distillation is carried out at a pressure at the top of the tower in the range of from 0.005 to 1.2 bar(abs), more preferably in the range of from 0.07 to 0.2 bar(abs) and a temperature at the bottoms of the tower in the range of from 110 to 175° C., more preferably in the range of from 130 to 155° C.

Side Stream S5

The side stream S5 (Si K1600) recovered from the distillation tower is enriched in the one or more solvents relative to the bottoms stream B3 (Su K1500). Preferably, at least 96 weight-%, more preferably from 99.0 to 99.9 weight-% of the side stream S5 (Si K1600) consist of the one or more solvents, based on the total weight-% of the side stream S5. Preferably, less than 50 weight-ppm, more preferably less than 20 weight-ppm of the side stream S5 consist of the high boilers. Preferably less than 20 weight-ppm, more preferably less than 5 weight-ppm of the side stream S5 consist of the middle boilers, more preferably the side stream S5 does not comprise middle boilers as defined above.

Preferably, the side stream S5 (Si K1600) is recovered at a temperature in the range of from 100 to 140° C., more preferably in the range of from 110 to 125° C.

Yield of the Process for Recovering MBE

As seen above the process as disclosed above avoids the loss of 3-methylbut-3-en-1-ol in the top stream T2. Advantageously, before being recycled in to the second distillation unit the stream T2 is depleted from part of water, of 3-methylbutane-1,3-diol, of the ester of formic acid and 3-methylbut-3-en-1-ol and/or of the low boiling solvents such as methanol and tert-butanol. Hence the 3-methylbut-3-en-1-ol is recycled purer in the second distillation unit.

Therefore according to the process disclosed above, 3-methylbut-3-en-1-ol is recovered in high purity and high percentage. Preferably at least 97 weight-%, more preferably at least 99.5 weight-% of the 3-methylbut-3-en-1-ol comprised in F1 are recovered in T3.

As seen above the process as disclosed above allows recovering the one or more solvents in high purity and high efficacy. In fact at least 96 weight-%, preferably from 99.0 to 99.9 weight-% of the side stream S5 (Si K1600) consist of the one or more solvents, based on the total weight-% of the side stream S5. Preferably at least 98 weight-%, more preferably at least 99.8 weight-% of the one or more solvents comprised in F1 are recovered in S5.

Hence the present invention is directed to a process for recovering 3-methylbut-3-en-1-ol and one or more solvents from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising the one or more solvents;
(iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq, wherein a portion PT2 (Reflux_K1300) and a portion L2or' (OP_Out) of the organic liquid stream L2or (B1310 OP) are separated from the organic liquid stream L2or (B1310 OP) and wherein the stream PT2 is fed back to the top of the distillation tower according to (ii);
(iv-a) subjecting the portion L2or' (OP_Out) and the stream L2aq (B 1310 WP) to distillation (K1400) in a fourth distillation unit, obtaining a side stream S2 (DSA) comprising 3-methylbut-3-en-1-ol and water, wherein the side stream S2 (DSA) is preferably fed back to the distillation according to (ii) (K1300);
(v) subjecting the bottoms stream B3 (Su K1500) to distillation (K1600) in a fifth distillation unit;
(vi) recovering a side stream S5 (Si K1600) comprising the one or more solvents from the fifth distillation unit,
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol and in the one or more solvent relative to the bottoms stream B1, wherein the top stream T3 (De K1500) is enriched in methylbut-3-en-1-ol relative to the bottoms stream B2 (Su K1300), wherein the bottoms stream B3 is enriched in the one or more solvents relative to the bottoms streams B1 and B2 and preferably wherein the one or more solvents comprises, more preferably is of 2-ethyl-hexanol. It is further preferred that (i) further comprises
(t) providing a mixture comprising formaldehyde, isobutene and the one or more solvents;
(tt) contacting the mixture provided in (t) with a condensation catalyst comprising, preferably consisting of an heterogeneous catalyst and obtaining the feed stream F1;

The heterogeneous catalyst is as defined herein above in the chapter A. Process for recovering methylbut-3-en-1-ol-Feed Stream F1 herein above.

Hence preferably the present invention is directed to a process for recovering 3-methylbut-3-en-1-ol and one or more solvents from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising the one or more solvents;
(iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq, wherein a portion PT2 (Reflux_K1300) and a portion L2or' (OP_Out) of the organic liquid stream L2or (B1310 OP) are separated from the organic liquid stream L2or (B1310 OP) and wherein the stream PT2 is fed back to the top of the distillation tower according to (ii);
(iv-a) subjecting the portion L2or' (OP_Out) and the stream L2aq (B 1310 WP) to distillation (K1400) in a fourth distillation unit, obtaining a side stream S2 (DSA) comprising 3-methylbut-3-en-1-ol and water, wherein the side stream S2 (DSA) is preferably fed back to the distillation according to (ii) (K1300);
(v) subjecting the bottoms stream B3 (Su K1500) to distillation (K1600) in a fifth distillation unit;
(vi) recovering a side stream S5 (Si K1600) comprising the one or more solvents from the fifth distillation unit,
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol and in the one or more solvent relative to the bottoms stream B1, wherein the top stream T3 (De K1500) is enriched in methylbut-3-en-1-ol relative to the bottoms stream B2(Su K1300), wherein the bottoms stream B3 is enriched in the one or more solvents relative to the bottoms streams B1 and B2 and preferably wherein the one or more solvents comprises, more preferably is of 2-ethyl-hexanol. It is further preferred that (i) further comprises (t) providing a mixture comprising formaldehyde, isobutene and the one or more solvents;
(tt) contacting the mixture provided in (t) with a condensation catalyst comprising a zeolitic material, obtaining the feed stream F1;
wherein the framework structure of the zeolitic material in (tt) comprises Si, 0, optionally Al, and a tetravalent element Y which is one or more of Sn, Ti and Zr, preferably Y is Sn wherein in the framework structure of the zeolitic material in (tt), the molar Al:Si ratio is in the range of from 0:1 to 0.001:1.

Hence the present invention is directed to a process for recovering 3-methylbut-3-en-1-ol, the one or more solvent and isobutene from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising the one or more solvents;
(iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq, wherein a portion PT2 (Reflux_K1300) and a portion L2or' (OP_Out) of the organic liquid stream L2or (B1310 OP) are separated from the organic liquid stream L2or (B1310 OP) and wherein the stream PT2 is fed back to the top of the distillation tower according to (ii);
(iv-a) subjecting the portion L2or' (OP_Out) and the stream L2aq (B 1310 WP) to distillation (K1400) in a fourth distillation unit, obtaining a side stream S2 (DSA) comprising 3-methylbut-3-en-1-ol and water, wherein the side stream S2 (DSA) is preferably fed back to the distillation according to (ii) (K1300)
(v) subjecting the bottoms stream B3 (Su K1500) to distillation (K1600) in a fifth distillation unit;
(vi) recovering a side stream S5 (Si K1600) from the fifth distillation unit, comprising the one or more solvents;
and the process further comprising recovering (W1210) the isobutene comprised in T1, wherein the recovery preferably comprises subjecting the top stream T1 (Br K1200) to heat exchange in a heat exchange unit (W1210), obtaining a condensed stream C6 (Kond W 1215) comprising isobutene; wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol and the one or more solvents relative to the bottoms stream B1, wherein the top stream T3 (De K1500) is enriched in methylbut-3-en-1-ol relative to the bottoms stream B2(Su K1300), wherein the bottoms stream B3 is enriched in the one or more solvents relative to the bottoms streams B1 and B2 and wherein the condensed stream C6 is enriched in isobutene with respect to the feed stream F1 and preferably wherein the one or more solvents comprises, more preferably is of 2-ethyl-hexanol. It is further preferred that (i) further comprises
(t) providing a mixture comprising formaldehyde, isobutene and the one or more solvents;
(tt) contacting the mixture provided in (t) with a condensation catalyst comprising, preferably consisting of an heterogeneous catalyst and obtaining the feed stream F1.

The heterogeneous catalyst is as defined herein above in the chapter A. Process for recovering methylbut-3-en-1-ol-Feed Stream F1 herein above.

Hence the present invention is directed to a process for recovering 3-methylbut-3-en-1-ol, the one or more solvent and isobutene from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising the one or more solvents;
(iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq, wherein a portion PT2 (Reflux_K1300) and a portion L2or' (OP_Out) of the organic liquid stream L2or (B1310 OP) are separated from the organic liquid stream L2or (B1310 OP) and wherein the stream PT2 is fed back to the top of the distillation tower according to (ii);
(iv-a) subjecting the portion L2or' (OP_Out) and the stream L2aq (B 1310 WP) to distillation (K1400) in a fourth distillation unit, obtaining a side stream S2 (DSA) comprising 3-methylbut-3-en-1-ol and water, wherein the side stream S2 (DSA) is preferably fed back to the distillation according to (ii) (K1300)
(v) subjecting the bottoms stream B3 (Su K1500) to distillation (K1600) in a fifth distillation unit;
(vi) recovering a side stream S5 (Si K1600) from the fifth distillation unit, comprising the one or more solvents;
and the process further comprising recovering (W1210) the isobutene comprised in T1, wherein the recovery preferably comprises subjecting the top stream T1 (Br K1200) to heat exchange in a heat exchange unit (W1210), obtaining a condensed stream C6 (Kond W 1215) comprising isobutene; wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol and the one or more solvents relative to the bottoms stream B1, wherein the top stream T3 (De K1500) is enriched in methylbut-3-en-1-ol relative to the bottoms stream B2(Su K1300), wherein the bottoms stream B3 is enriched in the one or more solvents relative to the bottoms streams B1 and B2 and wherein the condensed stream C6 is enriched in isobutene with respect to the feed stream F1 and preferably wherein the one or more solvents comprises, more preferably is of 2-ethyl-hexanol. It is further preferred that (i) further comprises (t) providing a mixture comprising formaldehyde isobutene and the one or more solvents;

(tt) contacting the mixture provided in (t) with a condensation catalyst comprising a zeolitic material, obtaining the feed stream F1;

wherein the framework structure of the zeolitic material in (tt) comprises Si, 0, optionally Al, and a tetravalent element Y which is one or more of Sn, Ti and Zr, preferably Y is Sn, wherein in the framework structure of the zeolitic material in (tt), the molar Al:Si ratio is in the range of from 0:1 to 0.001:1.

A.2 Process Wherein the One or More Solvents have a Boiling Point Lower than the Boiling Point of Methylbut-3-En-1-Ol The process for preparing 3-methylbut-3-en-1-ol as disclosed above can be carried out in one or more solvents that have a boiling point lower than 3-methylbut-3-en-1-ol. The recovery of the 3-methylbut-3-en-1-ol in this case requires a different sequence of distillation steps with respect to the higher boiling point solvents of aspect A.1 to assure the recovery of highly pure methylbut-3-en-1-ol with high efficiency.

Distillation Step (i) (K1200): Distillation of Feed Stream F1

As mentioned above the distillation of (i) has the purpose to separate isobutene from the feed stream F1. In the distillation step (i) a bottoms stream B1 enriched in 3-methylbut-3-en-1-ol, the one or more solvents and water and a top stream T1 enriched in isobutene compared to the feed stream F1 subjected to distillation conditions are formed.

According to (i), methylbut-3-en-1-ol, the one or more solvents and water are separated from the feed stream F1 by distillation, comprising subjecting the feed stream F1 to distillation conditions in a first distillation unit, preferably a distillation tower. From the distillation tower, a bottoms stream B1 enriched in methylbut-3-en-1-ol, the one or more solvents and water and a top stream T1 enriched in isobutene are obtained. Preferably B1 is obtained as liquid bottoms stream and T1 is obtained as gaseous top stream.

As to the distillation conditions, generally there is no particular restriction provided that a bottoms stream B1 and a top stream T1 as disclosed herein are obtained. Preferably, this distillation tower has from 7 to 30, more preferably 15 to 20 theoretical plates. The distillation tower is preferably operated at a top pressure in the range of from 4 to 20 bar(abs), more preferably in the range of from 7 to 13 bar(abs). The distillation tower is preferably operated at a temperature at the bottoms of the tower in the range of from 130 to 180° C., more preferably in the range of from 150 to 160° C. and at a temperature at the top of the tower in the range of from 40 to 90° C., more preferably in the range of from 60 to 70°.

Feed Stream F1

The feed stream F1 is as disclosed herein above in the general section. With regard to the one or more solvents comprised in the feed stream F1, generally, there is no specific restriction provided that they are suitable for the conversion of isobutene into 3-methylbut-3-en-1-ol in the presence of formaldehyde and preferably a zeolitic material as disclosed herein above and provided that the one or more solvents have a boiling point lower than the boiling point of 3-methylbut-3-en-1-ol wherein the boiling point of 3-methylbut-3-en-1-ol is in the range of from 130 to 132° C. Preferably the one or more solvents have a boiling point in the range of from 50 to 125° C., more preferably in the range of from 65 to 120° C., wherein the boiling points are at an absolute pressure of 1 bar.

It is further preferred that the one or more solvents is one or more of a secondary alcohol, a tertiary alcohol, a ketone, an ester and a nitrile. Preferably the secondary alcohol and the tertiary alcohol are one or more of methanol (65° C.), ethanol (78° C.), tert-butanol (82° C.), 2-propanol (83° C.), 1-propanol (97° C.), 2-methyl-2-butanol (102° C.), isobutanol (108° C.), 3-pentanol (115° C.), 1-butanol (118° C.), 2-pentanol (119° C.), more preferably one or more of tert-butanol (82° C.), 2-propanol (83° C.), 2-methyl-2-butanol (102° C.), isobutanol (108° C.), 3-pentanol (115° C.), 1-butanol (118° C.) and 2-pentanol (119° C.). Preferably, the ketone is one or more of acetone (56° C.), 2-butanon (80° C.) and 2-pentanon (102° C.). Preferably, the ester is ethyl acetate (77° C.) and preferably the nitrile is acetonitrile.

The boiling points in parenthesis are indicative values to show that the solvent mentioned meets the requirement of having a boiling point lower than the boiling point of 3-methylbut-3-en-1-ol. They are not meant to limit the scope of the present invention.

Bottoms Stream B1

The bottoms stream B1 is recovered from the bottom plate of the first distillation unit. Generally, there is no specific restriction with respect to the composition of the bottoms stream B1, provided that it comprises methylbut-3-en-1-ol, the one or more solvents and water and is enriched in methylbut-3-en-1-ol, the one or more solvents and water and is depleted in isobutene compared to the feed stream F1 subjected to distillation conditions. Preferably at least 10 weight-%, more preferably from 15 to 30 weight-% of the bottoms stream B1 (Su K1200) consist of methylbut-3-en-1-ol, preferably at least 50 weight-%, more preferably from 60 to 80 weight-% of the bottoms stream B1 (Su K1200) consist in the one or more solvents, preferably at least 3 weight-%, more preferably from 5 to 9 weight-% of the bottoms stream B1 (Su K1200) consist of water and preferably less than 0.1 weight-%, more preferably from 0.01 to 0.1 weight-% of the bottoms stream B1 consist of isobutene. It conceived that at least 96 weight-%, preferably from 97 to 99 weight-% of the bottoms stream B1 consist of 3-methylbut-3-en-1-ol, the one or more solvents and water. The percentage values are in each case based on the total weight of the bottoms stream B1.

It is conceivable that in addition to 3-methylbut-3-en-1-ol, the one or more solvents and water, the bottoms stream B1 optionally comprises other compounds that were optionally comprised in the feed stream F1. For example, the bottoms stream B1 may further comprise one or more of 3-methylbutane-1,3-diol and the ester of formic acid and 3-methylbut-3-en-1-ol. It is conceived that these products, if present, are present in small amounts in the bottoms stream B1. It is conceived that at most 2 weight-%, preferably at most 1.5 weight-% of the bottoms stream B1 consist of 3-methylbutane-1,3-diol. It is conceived that at least the 99.5 weight-%, preferably at least the 99.9 weight-% of the 3-methylbutane-1,3-diol comprised in the feed stream F1 is recovered in the bottoms stream B1. It is conceived that at most 1 weight-%, preferably at most 0.5 weight-% of the bottoms stream B1 consist of the ester of formic acid and 3-methylbut-3-en-1-ol. It is conceived that at least the 99.5 weight-%, preferably at least the 99.9 weight-% of the ester of formic acid and 3-methylbut-3-en-1-ol comprised in the feed stream F1 is recovered in the bottoms stream B1

With regard to the one or more solvents of the bottoms stream B1, the one or more solvents have a boiling point lower than the boiling point of 3-methylbut-3-en-1-ol, wherein the boiling point of 3-methylbut-3-en-1-ol is in the range of from 130 to 132° C. at an absolute pressure of 1 bar and are as disclosed herein above.

Top Stream T1

According to (i), isobutene is separated from the feed stream F1 in a distillation unit as disclosed above. Generally there is no particular restriction as to the top stream T1, provided that it is enriched in isobutene with respect to the feed stream F1 Preferably at least 92 weight-%, more preferably from 97 to 99.9 weight-%, more preferably 98 to 99.6 weight-% of the top stream T1 (Br K1200) consist of isobutene, based on the total weight of the top stream T1 (Br K1200). It is contemplated that optionally less than 0.7 weight-%, preferably less than 0.5 weight-% of the top stream T1 consist of the one or more solvents.

Preferably the top stream T1 has a temperature in the range of from 40 to 90° C., preferably in the range of from 60 to 70° C., and a pressure in the range of from 3 to 25 bar(abs), preferably in the range of from 7 to 13 bar(abs).

Distillation Step (ii) (K1300): Distillation of the Bottoms Stream B1

According to step (ii) the bottoms stream B1 (Su K1200) is subjected to distillation in a second distillation unit (K1300), a bottoms stream B2 (Su K1300) enriched in 3-methylbut-3-en-1-ol and a top stream T2 (De K1300) enriched in the one or more solvents and water are obtained. The purpose of step (ii) is to separate the one or more solvents and water from the 3-methylbut-3-en-1-ol. The step efficiently separates 3-methylbut-3-en-1-ol from the one or more solvents and water.

According to (ii), 3-methylbut-3-en-1-ol is separated from the one or more solvents and water by distillation, comprising subjecting the bottoms stream B1 to distillation conditions in a second distillation unit, preferably a distillation tower. From the distillation tower, a bottoms stream B2 enriched in methylbut-3-en-1-ol and a top stream T2 enriched in water and the one or more solvents both streams compared to the bottoms stream B1 are obtained. Preferably, the bottoms stream B2 is obtained as liquid bottoms stream and the top stream T2 is obtained as liquid top stream.

As to the distillation conditions, generally there is no particular restriction provided that a bottoms stream B2 and a top stream T2 as disclosed herein are obtained. Preferably, this distillation tower has from 10 to 50, more preferably 25 to 35 theoretical plates. The distillation tower is preferably operated at a top pressure in the range of from 0.05 to 3 bar(abs), more preferably in the range of from 0.5 to 1.5 bar(abs).The distillation tower is preferably operated at a temperature at the bottoms of the tower in the range of from 130 to 155° C., more preferably in the range of from 130 to 140° C. and at a temperature at the top of the tower in the range of from 60 to 95° C., more preferably in the range of from 75 to 85° C.

Bottoms Stream B2

Generally, there is no specific restriction with respect to the composition of the bottoms stream B2, provided that it is enriched in methylbut-3-en-1-ol and is depleted in water and the one or more solvents compared to the bottoms stream B1 subjected to distillation conditions. Preferably at least 84 weight-%, more preferably from 93 to 95 weight-% of the bottoms stream B2 (Su K1300) consist of methylbut-3-en-1-ol, preferably less than 0.25 weight-%, more preferably from 0.01 to 0.1 weight-% of the bottoms stream B2 (Su K1300) consist of the one or more solvents, preferably less than 0.3 weight-%, more preferably from 0.01 to 0.1 weight-% of the bottoms stream B2 (Su K1300) consist of water, in each case based on the total weight of the bottoms stream B2.

Optionally the bottoms stream B2 comprises 3-methylbutane-1,3-diol. Preferably, less than 7 weight-%, more preferably less than 6 weight-% of the bottoms stream B2 consist of 3-methylbutane-1,3-diol. It is conceived that at least the 99.5 weight-%, preferably at least the 99.9 weight-% of the 3-methylbutane-1,3-diol comprised in the bottoms stream B1 is recovered in the bottoms stream B2.

Optionally the bottoms stream B2 comprises the ester of formic acid and 3-methylbut-3-en-1-ol. Preferably, less than 600 weight-ppm, more preferably less than 500 weight-ppm of the bottoms stream B2 consist of the ester of formic acid and 3-methylbut-3-en-1-ol.

Top Stream T2 (Solvent Recovery)

Generally, there is no specific restriction with respect to the composition of the top stream T2, provided that is enriched in the water and in the one or more solvents and is depleted of methylbut-3-en-1-ol compared to the bottoms stream B1 subjected to distillation conditions. Preferably at least 70 weight-%, more preferably from 85 to 95 weight-% of the top stream T2 (De K1300) consist of the one or more solvents, preferably at least 4 weight-%, more preferably from 9 to 12 weight-% of the top stream T2 (De K1300) consist of water, and preferably less than 2 weight-%, more preferably from 0.5 to 0.05 weight-% of the top stream T2 (De K1300) consist of 3-methylbut-3-en-1-ol, in each case based on the total weight of the top stream T2.

Optionally the top stream T2 comprises the ester of formic acid and 3-methylbut-3-en-1-ol. Preferably, less than 0.7 weight-%, more preferably less than 0.4 weight-% of the top stream T2 consist of the ester of formic acid and 3-methylbut-3-en-1-ol. It is conceived that at least the 94 weight-%, preferably at least the 96 weight-% of the ester of formic acid and 3-methylbut-3-en-1-ol comprised in the feed stream F1 is recovered via the top stream T2.

In dependence on the one or more solvents it is conceived that the top stream T2 (De K1300) comprises water and the one or more solvents, wherein water and the one or more solvents may form an azeotrope. Preferably, the top stream T2 is an azeotropic mixture comprising methanol and tert-butanol wherein preferably this azeotropic mixture comprises from 75 to 95 weight-% tert-butanol, from 0.05 to 2 weight-% methanol and from 3 to 15 weight-% water, more preferably from 88 to 92 weight-% of tert-butanol, from 0.2 to 0.8 weight-% of methanol and from 8 to 11 weight-% water. It is contemplated that the top stream T2 is further subjected to an azeotropic distillation to further separate the solvents and the water.

Vapor-Liquid Separation of the Bottoms Stream B1 (B1300_Flash)

To render more efficient the separation process it is contemplated that the bottoms stream B1 after (i) and prior to (ii) is preferably subjected to a vapor-liquid separation (B1300_Flash) in a phase separation unit. A top stream T7 (B1300_Fl) and a bottoms stream B7 (B1300_Gas) are obtained. The top stream T7 is richer in 3-methylbut-3-en-1-ol than the gas stream G7. The bottoms stream B7 and the top stream T7 are then subjected to distillation according to (ii). Preferably, the bottoms stream B7 and the top stream T7 are fed at the side of the distillation unit of (ii).

Generally there is no restriction as to the conditions of the vapor-liquid separation provided that the stream T7 and G7 as disclosed above obtained, wherein top stream T7 is richer in 3-methylbut-3-en-1-ol than the gas stream G7. Preferably, the vapor-liquid separation (B1300_Flash) is carried out at a temperature in the range of from 80 to 150° C., more preferably in the range of from 100 to 130° C. Preferably the vapor-liquid separation (B1300_Flash) is carried out at a pressure in the range of from 0.05 to 3 bar(abs), more preferably in the range of from 0.5 to 1.5 bar(abs).

Distillation Step (iii) (K1500): Distillation of the Bottoms Stream B2

According to step (iii) the bottoms stream B2 (Su K1300) is subjected to distillation in a third distillation unit (K1500), a top stream T3 (De K1500) enriched in 3-methylbut-3-en-1-ol and a bottoms stream B3 (Su K1500) comprising of 3-methylbutane-1,3-diol are obtained.

The purpose of step (iii) is to separate the 3-methylbut-3-en-1-ol from 3-methylbutane-1,3-diol comprised in the bottoms stream B2, thereby enriching the top stream T3 in highly pure 3-methylbut-3-en-1-ol. The process is highly efficient since at least 98 weight-%, more preferably at least 99.5 weight-% of the 3-methylbut-3-en-1-ol comprised in the feed stream F1 is recovered in T3. The process also provides pure 3-methylbut-3-en-1-ol as at least 98 weight-%, preferably from 99.5 to 99.95 weight-%, more preferably from 99.8 to 99.9 weight-% of the top stream T3 (De K1500) consist of 3-methylbut-3-en-1-ol.

According to (iii), 3-methylbut-3-en-1-ol is separated from the 3-methylbutane-1,3-diol by distillation, comprising subjecting the bottoms stream B2 to distillation conditions in a third distillation unit, preferably a distillation tower. From the distillation tower, a top stream T3 enriched in methylbut-3-en-1-ol compared to the bottoms stream B2 and a bottoms stream B3 enriched in 3-methylbut-3-en-1-ol are obtained. Preferably the top stream T3 is obtained as liquid top stream.

As to the distillation conditions, generally there is no particular restriction provided that a bottoms stream B3 and a top stream T3 as disclosed herein are obtained. Preferably, this distillation tower has from 4 to 25, more preferably from 7 to 12 theoretical plates. The distillation tower is preferably operated at a top pressure in the range of from 0.03 to 1.4 bar(abs), more preferably in the range of from 0.09 to 0.5 bar(abs). The distillation tower is preferably operated at a temperature at the bottoms of the tower in the range of from 120 to 170° C., more preferably in the range of from 140 to 150° C. and at a temperature at the top of the tower in the range of from 45 to 95° C., more preferably in the range of from 65 to 75° C.

Top Stream T3 (De K1500) (3-Methylbut-3-En-1-Ol Pure)

The top stream T3 is recovered from the top of the third distillation unit. It is conceived that at least 98 weight-%, preferably from 99.5 to 99.95 weight-%, more preferably from 99.8 to 99.9 weight-% of the top stream T3 (De K1500) consist of 3-methylbut-3-en-1-ol. It is conceived that less than 700 ppm (0.07 weight-%), preferably from 50 to 0.5 ppm (0.005 to 0.00005 weight-%), more preferably from 20 to 1 ppm (0.002 to 0.0001 weight-%) of the top stream T3 (De K1500) consist of the one or more solvents, in each case based on the total weight of the top stream T3. It is conceived that less than 10 weight-ppm of the top stream T3, preferably less than 6 weight-ppm of the top stream T3 consists of 3-methylbutane-1,3-diol based on the total weight of the top stream T3. It is conceived that less than 600 weight-ppm of the top stream T3, preferably less than 550 weight-ppm of the top stream T3 consists of the ester of formic acid and 3-methylbut-3-en-1-ol based on the total weight of the top stream T3.

Vapor-Liquid Separation of the Bottoms Stream B2 (B1500)

To render more efficient the separation process it is contemplated that the bottoms stream B2 after (ii) and prior to (iii) is preferably subjected to a vapor-liquid separation (B1500) in a phase separation unit. A liquid stream L8 (B1500_Fl) and a gas stream G8; (B1500_Br) are obtained. The gas stream G8 and the liquid stream L8 are then subjected to distillation according to (iii). Generally, the gas stream G8 and the liquid stream L8 are fed at the side of the third distillation unit.

Generally there is no restriction as to the conditions of the vapor-liquid separation. Preferably, the vapor-liquid separation (B1500) is carried out at a temperature in the range of from 80 to 120° C., more preferably in the range of from 90 to 105° C. Preferably the vapor-liquid separation (B1500) is carried out at a pressure in the range of from 0.01 to 0.5 bar(abs), more preferably in the range of from 0.08 to 0.2 bar(abs).

Yield of the Process for Recovering MBE

Therefore according to the process disclosed above, the 3-methylbut-3-en-1-ol is recovered in high purity as least 98 weight-%, preferably from 99.5 to 99.95 weight-%, more preferably from 99.8 to 99.9 weight-% of the top stream T3 (De K1500) consist of 3-methylbut-3-en-1-ol. Therefore according to the process disclosed above, the 3-methylbut-3-en-1-ol is recovered in high amount as at least 98 weight-%, preferably at least 99.5 weight-% of the 3-methylbut-3-en-1-ol comprised in F1 is recovered in T3.

Therefore according to the process of the invention the one or more solvents are recovered in high amount as at least 98 weight-%, preferably at least 99.6 weight-% of the one or more solvents comprised in F1 is recovered via T2.

Therefore, the present invention relates to a process for recovering 3-methylbut-3-en-1-ol from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and a top stream T2 (De K1300) comprising water and the one or more solvents;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500);
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol relative to the bottoms stream B1, wherein the top stream T3 (De K1500) is enriched in methylbut-3-en-1-ol relative to the bottoms stream B2 (Su K1300) and wherein the top stream T2 is enriched in the one or more solvents and water relative to the bottoms stream B1 and preferably wherein the one or more solvents comprises, more preferably is a mixture of methanol and tert butanol. It is further preferred that (i) further comprises (t) providing a mixture comprising formaldehyde, isobutene and the one or more solvents;

(tt) contacting the mixture provided in (t) with a condensation catalyst comprising, preferably consisting of an heterogeneous catalyst and obtaining the feed stream F1.

The heterogeneous catalyst is as defined herein above in the chapter A. Process for recovering methylbut-3-en-1-ol-Feed Stream F1 herein above.

Therefore, the present invention relates to a process for recovering 3-methylbut-3-en-1-ol from a feed stream F1 comprising 3-methylbut-3-en-1-ol, one or more solvents, water, and isobutene, the process comprising (i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;

(ii) subjecting the bottoms stream B1 (Su K1200) to distillation in a second distillation unit (K1300), obtaining a bottoms stream B2 (Su K1300) comprising 3-methylbut-3-en-1-ol and a top stream T2 (De K1300) comprising water and the one or more solvents;

(iii) subjecting the bottoms stream B2 to distillation in a third distillation unit (K1500), obtaining a top stream T3 (De K1500) comprising 3-methylbut-3-en-1-ol and a bottoms stream B3 (Su K1500);

wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol relative to the bottoms stream B1, wherein the top stream T3 (De K1500) is enriched in methylbut-3-en-1-ol relative to the bottoms stream B2 (Su K1300) and wherein the top stream T2 is enriched in the one or more solvents and water relative to the bottoms stream B1 and preferably wherein the one or more solvents comprises, more preferably is a mixture of methanol and tert butanol. It is further preferred that (i) further comprises (t) providing a mixture comprising formaldehyde and isobutene and the one or more solvents;

(tt) contacting the mixture provided in (t) with a condensation catalyst comprising a zeolitic material, obtaining the feed stream F1;

wherein the framework structure of the zeolitic material in (tt) comprises Si, 0, optionally Al, and a tetravalent element Y which is one or more of Sn, Ti and Zr, preferably Y is Sn, wherein in the framework structure of the zeolitic material in (tt), the molar Al:Si ratio is in the range of from 0:1 to 0.001:1.

B. Recovery of Isobutene

As mentioned above in both aspects A.1 and A.2 of the invention the process may further comprise the recovery of the unreacted isobutene. As disclosed above isobutene is separated from the 3-methylbut-3-en-1-ol, the one of more solvents and water comprised in the feed stream F1, by the distillation step (i) wherein isobutene is comprised in the top stream T1. The process further involves the use of a heat exchanger to condensate the gaseous top stream T1 in a condensate liquid stream. Part of this condensed liquid stream is returned to the top of first distillation unit as reflux stream. Inside the column the downflowing reflux liquid provides cooling and condensation of the upflowing vapors thereby increasing the efficiency of the separation of the isobutene from 3-methylbut-3-en-1-ol, the one or more solvents and water.

Hence, the process according to aspects A.1 and A.2 preferably comprises recovering (W1210) the isobutene, wherein the recovery preferably comprises subjecting the top stream T1 (Br K1200) to heat exchange in a heat exchange unit (W1210), obtaining a condensed stream C6 (Kond W 1215) comprising isobutene. Preferably the process further comprises separating a portion PT1 (Reflux_K1200) and a portion PT1' (Out_W1215) of the condensed stream C6 from C6 and feeding PT1 back to the top of the distillation tower according to (i), wherein PT1 is preferably in the range of from 20 to 75 weight-%, more preferably in the range of from 40 to 50 weight-% of T1 based in the total weight of T1.

It is further contemplated that PT1 is preferably in the range of from 20 to 75 weight-%, more preferably in the range of from 40 to 50 weight-% of the condensed stream C6, based in the total weight of C6.

The process is highly efficient as at least 97 weight-%, preferably at least 99.6 weight-% of the isobutene comprised in F1 is recovered via T1, based on the total weight of T1, preferably from PT1', based on the total weight of PT1'.

The specific compositions of the top stream T1 according to A.1 and A.2 are as disclosed above.

Condensed Stream C6 and the Portions PT1 and PT1'

Generally there is no particular restriction as to the condensed stream C6 and the portions PT1 and PT1', provided that they are enriched in isobutene with respect to the feed stream F1. Preferably, at least 92 weight-%, more preferably from 97 to 99.9 weight-%, more preferably 98 to 99.6 weight-% of the condensed stream C6 consist of isobutene, based on the total weight of the condensed stream C6.

Preferably, at least 92 weight-%, more preferably from 97 to 99.9 weight-%, more preferably 98 to 99.6 weight-% of the portion PT1 consist of isobutene, based on the total weight of the portion PT1. Preferably, at least 92 weight-%, more preferably from 97 to 99.9 weight-%, more preferably 98 to 99.6 weight-% of the portion PT1' consist of isobutene, based on the total weight of the portion PT1'.

It is contemplated that less than 0.7 weight-%, preferably less than 0.5 weight-% of condensed stream C6 consist of the one or more solvents based on the total weight of the condensed stream C6. is contemplated that less than 0.7 weight-%, preferably less than 0.5 weight-% of portion PT1 consist of the one or more solvents based on the total weight of the portion PT1. It is contemplated that less than 0.7 weight-%, preferably less than 0.5 weight-% of portion PT1' consist of the one or more solvents based on the total weight of the portion PT1'.

Hence the present invention is directed to a process for recovering 3-methylbut-3-en-1-ol, the one or more solvent and isobutene from a feed stream F1 comprising 3-methylbut-3-en-1-ol, one or more solvents, water, and isobutene, the process comprising (i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;

(ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water;

(iii) subjecting the bottoms stream B2 to distillation in a third distillation unit (K1500), obtaining a top stream T3

(De K1500) comprising 3-methylbut-3-en-1-ol and a bottoms stream B3 (Su K1500) comprising the one or more solvents;
(iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq, wherein a portion PT2 (Reflux_K1300) and a portion L2or' (OP_Out) of the organic liquid stream L2or (B1310 OP) are separated from the organic liquid stream L2or (B1310 OP) and wherein the stream PT2 is fed back to the top of the distillation tower according to (ii);
(iv-a) subjecting the portion L2or' (OP_Out) and the stream L2aq (B 1310 WP) to distillation (K1400) in a fourth distillation unit, obtaining a side stream S2 (DSA) comprising 3-methylbut-3-en-1-ol and water, wherein the side stream S2 (DSA) is preferably fed back to the distillation according to (ii) (K1300);
(v) subjecting the bottoms stream B3 (Su K1500) to distillation (K1600) in a fifth distillation unit;
(vi) recovering a side stream S5 (Si K1600) from the fifth distillation unit, comprising the one or more solvents and the process further comprising recovering (W1210) the isobutene comprised in T1, wherein the recovery preferably comprises subjecting the top stream T1 (Br K1200) to heat exchange in a heat exchange unit (W1210), obtaining a condensed stream C6 (Kond W 1215) comprising isobutene;
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol and the one or more solvents relative to the bottoms stream B1, wherein the top stream T3 (De K1500) is enriched in methylbut-3-en-1-ol relative to the bottoms stream B2(Su K1300), wherein the bottoms stream B3 is enriched in the one or more solvents relative to the bottoms streams B1 and B2 and wherein the condensed stream C6 is enriched in isobutene with respect to the feed stream F1 and preferably wherein the one or more solvents comprises, more preferably is of 2-ethyl-hexanol. It is further preferred that (i) further comprises
(t) providing a mixture comprising formaldehyde, isobutene and the one or more solvents;
(tt) contacting the mixture provided in (t) with a condensation catalyst comprising, preferably consisting of an heterogeneous catalyst and obtaining the feed stream F1.

The heterogeneous catalyst is as defined herein above in the chapter A. Process for recovering methylbut-3-en-1-ol-Feed Stream F1 herein above.

Hence the present invention is directed to a process for recovering 3-methylbut-3-en-1-ol, the one or more solvent and isobutene from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising the one or more solvents;
the process further comprising
recovering (W1210) the isobutene comprised in T1, wherein the recovery preferably comprises subjecting the top stream T1 (Br K1200) to heat exchange in a heat exchange unit (W1210), obtaining a condensed stream C6 (Kond W 1215) comprising isobutene;
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol and the one or more solvents relative to the bottoms stream B1, wherein the top stream T3 (De K1500) is enriched in methylbut-3-en-1-ol relative to the bottoms stream B2(Su K1300), wherein the bottoms stream B3 is enriched in the one or more solvents relative to the bottoms streams B1 and B2 and wherein the condensed stream C6 is enriched in isobutene with respect to the feed stream F1 and preferably wherein the one or more solvents comprises, more preferably is of 2-ethyl-hexanol. It is further preferred that (i) further comprises
(t) providing a mixture comprising formaldehyde, isobutene and the one or more solvents;
(tt) contacting the mixture provided in (t) with a condensation catalyst comprising, preferably consisting of an heterogeneous catalyst and obtaining the feed stream F1.

The heterogeneous catalyst is as defined herein above in the chapter A. Process for recovering methylbut-3-en-1-ol-Feed Stream F1 herein above.

Therefore, the present invention relates to a process for recovering 3-methylbut-3-en-1-ol and isobutene from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, the one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and a top stream T2 (De K1300) comprising water and the one or more solvents;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500);
the process further comprising
recovering (W1210) the isobutene comprised in T1, wherein the recovery preferably comprises subjecting the top stream T1 (Br K1200) to heat exchange in a heat exchange unit (W1210), obtaining a condensed stream C6 (Kond W 1215) comprising isobutene;
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol relative to the bottoms stream B1, wherein the top stream T3 (De K1500) is enriched in methylbut- 3-en-1-ol relative to the bottoms stream B2 (Su K1300) and wherein the top stream T2 is enriched in the one or more solvents and water relative to the bottoms stream B1 and wherein the condensed stream C6 is enriched in isobutene with respect to the feed stream F1 and preferably wherein the one or more solvents comprises, more preferably is a mixture of methanol and tert-butanol. It is further preferred that (i) further comprises
(t) providing a mixture comprising formaldehyde, isobutene and the one or more solvents;
(tt) contacting the mixture provided in (t) with a condensation catalyst comprising, preferably consisting of an heterogeneous catalyst and obtaining the feed stream F1;

The heterogeneous catalyst is as defined herein above in the chapter A. Process for recovering methylbut-3-en-1-ol-Feed Stream F1 herein above.

Hence preferably the present invention is directed to a process for recovering 3-methylbut-3-en-1-ol, the one or more solvent and isobutene from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising the one or more solvents;
(iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq, wherein a portion PT2 (Reflux_K1300) and a portion L2or' (OP_Out) of the organic liquid stream L2or (B1310 OP) are separated from the organic liquid stream L2or (B1310 OP) and wherein the stream PT2 is fed back to the top of the distillation tower according to (ii);
(iv-a) subjecting the portion L2or' (OP_Out) and the stream L2aq (B 1310 WP) to distillation (K1400) in a fourth distillation unit, obtaining a side stream S2 (DSA) comprising 3-methylbut-3-en-1-ol and water, wherein the side stream S2 (DSA) is preferably fed back to the distillation according to (ii) (K1300)
(v) subjecting the bottoms stream B3 (Su K1500) to distillation (K1600) in a fifth distillation unit;
(vi) recovering a side stream S5 (Si K1600) from the fifth distillation unit, comprising the one or more solvents and the process further comprising recovering (W1210) the isobutene comprised in T1, wherein the recovery preferably comprises subjecting the top stream T1 (Br K1200) to heat exchange in a heat exchange unit (W1210), obtaining a condensed stream C6 (Kond W 1215) comprising isobutene;
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol and the one or more solvents relative to the bottoms stream B1, wherein the top stream T3 (De K1500) is enriched in methylbut-3-en-1-ol relative to the bottoms stream B2(Su K1300), wherein the bottoms stream B3 is enriched in the one or more solvents relative to the bottoms streams B1 and B2 and wherein the condensed stream C6 is enriched in isobutene with respect to the feed stream F1 and preferably wherein the one or more solvents comprises, more preferably is of 2-ethyl-hexanol. It is further preferred that (i) further comprises
(t) providing a mixture comprising formaldehyde isobutene and the one or more solvents;
(tt) contacting the mixture provided in (t) with a condensation catalyst comprising a zeolitic material, obtaining the feed stream F1;
wherein the framework structure of the zeolitic material in (tt) comprises Si, O, optionally Al, and a tetravalent element Y which is one or more of Sn, Ti and Zr, preferably Y is Sn, wherein in the framework structure of the zeolitic material in (tt), the molar Al:Si ratio is in the range of from 0:1 to 0.001:1.

Hence the present invention is directed to a process for recovering 3-methylbut-3-en-1-ol, the one or more solvent and isobutene from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and the one or more solvents and a top stream T2 (De K1300) comprising water;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising the one or more solvents;
the process further comprising
recovering (W1210) the isobutene comprised in T1, wherein the recovery preferably comprises subjecting the top stream T1 (Br K1200) to heat exchange in a heat exchange unit (W1210), obtaining a condensed stream C6 (Kond W 1215) comprising isobutene;
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol and the one or more solvents relative to the bottoms stream B1, wherein the top stream T3 (De K1500) is enriched in methylbut-3-en-1-ol relative to the bottoms stream B2(Su K1300), wherein the bottoms stream B3 is enriched in the one or more solvents relative to the bottoms streams B1 and B2 and wherein the condensed stream C6 is enriched in isobutene with respect to the feed stream F1 and preferably wherein the one or more solvents comprises, more preferably is of 2-ethyl-hexanol. It is further preferred that (i) further comprises
(t) providing a mixture comprising formaldehyde isobutene and the one or more solvents;

(tt) contacting the mixture provided in (t) with a condensation catalyst comprising a zeolitic material, obtaining the feed stream F1;
wherein the framework structure of the zeolitic material in (tt) comprises Si, O, optionally Al, and a tetravalent element Y which is one or more of Sn, Ti and Zr, preferably Y is Sn, wherein in the framework structure of the zeolitic material in (tt), the molar Al:Si ratio is in the range of from 0:1 to 0.001:1.

Therefore, the present invention relates to a process for recovering 3-methylbut-3-en-1-ol and isobutene from a feed stream F1 comprising 3-methylbut-3-en-1-ol, one or more solvents, water, and isobutene, the process comprising
(i) subjecting a feed stream F1 to distillation in a first distillation unit (K1200), obtaining a bottoms stream B1 (Su K1200) comprising 3-methylbut-3-en-1-ol, the one or more solvents and water, and a top stream T1 (De K1200) comprising isobutene;
(ii) subjecting the bottoms stream B1 (Su K1200) to distillation in a second distillation unit (K1300), obtaining a bottoms stream B2 (Su K1300) comprising 3-methylbut-3-en-1-ol and a top stream T2 (De K1300) comprising water and the one or more solvents;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500);
the process further comprising
recovering (W1210) the isobutene comprised in T1, wherein the recovery preferably comprises subjecting the top stream T1 (Br K1200) to heat exchange in a heat exchange unit (W1210), obtaining a condensed stream C6 (Kond W 1215) comprising isobutene;
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol relative to the bottoms stream B1, wherein the top stream T3 (De K1500) is enriched in methylbut-3-en-1-ol relative to the bottoms stream B2 (Su K1300) and wherein the top stream T2 is enriched in the one or more solvents and water relative to the bottoms stream B1 and wherein the condensed stream C6 is enriched in isobutene with respect to the feed stream F1 and preferably wherein the one or more solvents comprises, more preferably is a mixture of methanol and tert-butanol. It is further preferred that (i) further comprises
(t) providing a mixture comprising formaldehyde, isobutene and the one or more solvents;
(tt) contacting the mixture provided in (t) with a condensation catalyst comprising a zeolitic material, obtaining the feed stream F1;
wherein the framework structure of the zeolitic material in (tt) comprises Si, O, optionally Al, and a tetravalent element Y which is one or more of Sn, Ti and Zr, preferably Y is Sn, wherein in the framework structure of the zeolitic material in (tt), the molar Al:Si ratio is in the range of from 0:1 to 0.001:1.

Composition Comprising 3-Methylbut-3-En-1 and Used Thereof

The present invention is further directed to a composition comprising 3-methylbut-3-en-1-ol, wherein at least 99 weight-%, preferably from 99.5 to 99.99 weight-%, more preferably from 99.8 to 99.9 weight-% of said composition consist of 3-methylbut-3-en-1-ol and wherein the composition is obtainable or obtained as top stream T3 by a process as disclosed herein above.

The composition of the top stream T3 can be used for the desired purpose without further purification. 3-methylbut-3-en-1-ol also known as isoprenol is an important intermediate in the chemical industry. Isoprenol is an important monomeric starting material for preparing 3,7-dimethyl-2,6-octadienal (citral) and/or the E-isomer of 3,7-dimethyl-2,6-octadienal (geranial) and/or the Z-isomer of 3,7-dimethyl-2,6-octadienal (neral). Citral, geranial and neral are commonly used as aroma chemical compounds. The composition of the top stream T3 can be used as a starting material for preparing a monomeric, oligomeric or polymeric compound, preferably as a starting material for preparing a monomeric, oligomeric or polymeric compound, preferably as a starting material for preparing an aroma chemical, preferably one or more of 3,7-dimethyl-2,6-octadienal (Citral), 2-isobutyl-4-hydroxy-4-methyl tetrahydropyran (Pyranol), or as a starting material for preparing an isoprenol polyether derivative as a component of a copolymer which is suitable as a superplasticizer for a hydraulic binder. Preferably, the composition of the top stream T3 is used as a starting material for preparing the E-isomer of 3,7-dimethyl-2,6-octadienal (geranial) or the Z-isomer of 3,7-dimethyl-2,6-octadienal (neral) or a mixture of said E-isomer and said Z-isomer, preferably a racemic mixture thereof (citral), wherein one or more thereof are preferably used as an aroma chemical compound. Citral, for example, can be further used as a starting material for preparing terpenic aroma chemicals, for example citronellol, geraniol, or L-menthol. Yet further, citral can be used as a building block in the synthesis if Vitamin A or Vitamin E. With regard to the use as a starting material for preparing Pyranol, reference is made, for example, to the respective disclosure in US 2012059177 A, WO 2011/154330 A and WO 2011/147919 A. With regard to the use as a starting material for preparing an isoprenol polyether derivative, reference is made, for example, to the respective disclosure in US 2011054083 A where such copolymers and their preparation is described, said copolymers comprising 5-55 mol-% of said isoprenol polyether derivative structural unit alpha, 2-90 mol-% of an acrylic acid derivative structural unit beta, and 2-90 mol-% of a hydroxyalkyl acrylate structural unit gamma. Specifically, said isoprenol polyether derivative structural unit alpha is represented by the formula —(CH$_2$—C(CH$_3$)((C$_2$H$_4$—O-(A-O)$_a$—H))— wherein A are as defined in US 2011054083 A.

The present invention is further illustrated by the following embodiments and combinations of embodiments as indicated by the respective dependencies and back-references. In particular, it is noted that in each instance where reference is made to more than two embodiments, for example in the context of a term such as "The process of any one of embodiments 1 to 4", every embodiment in this range is meant to be explicitly disclosed, i.e. the wording of this term is to be understood as being synonymous to "The process of any one of embodiments 1, 2, 3, and 4".

1. A process for recovering 3-methylbut-3-en-1-ol from a feed stream F1 comprising 3-methylbut-3-en-1-ol, one or more solvents, water, and isobutene, the process comprising
    (i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
    (ii) subjecting the bottoms stream B1 (Su K1200) to distillation in a second distillation unit (K1300), obtaining a bottoms stream B2 (Su K1300) comprising 3-methylbut-3-en-1-ol and a top stream T2 (De K1300) comprising water;
(iii) subjecting the bottoms stream B2 to distillation in a third distillation unit (K1500), obtaining a top stream T3 (De K1500) comprising 3-methylbut-3-en-1-ol and a bottoms stream B3 (Su K1500);
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol relative to the bottoms stream B1, wherein the top stream T3 (De K1500) is enriched in methylbut-3-en-1-ol relative to the bottoms stream B2(Su K1300).

2. The process of embodiment 1, wherein the feed stream F1 (feed_K1200) is a reaction mixture obtainable or obtained by a method for preparing of 3-methylbut-3-en-1-ol, said method comprising
(t) providing a mixture comprising formaldehyde, isobutene and the one or more solvents;
(tt) contacting the mixture provided in (t) with a condensation catalyst comprising a zeolitic material, obtaining the feed stream F1;
wherein the framework structure of the zeolitic material in (tt) comprises Si, O, optionally Al, and a tetravalent element Y which is one or more of Sn, Ti and Zr, wherein in the framework structure of the zeolitic material in (tt), the molar Al:Si ratio is in the range of from 0:1 to 0.001:1.

3. The process of embodiment 1, wherein prior to (i), the process comprises
(t) providing a mixture comprising formaldehyde, isobutene and the one or more solvents;
(tt) contacting the mixture provided in (t) with a condensation catalyst comprising a zeolitic material, obtaining the feed stream F1;
wherein the framework structure of the zeolitic material according to (tt) comprises Si, O, optionally Al, and a tetravalent element Y which is one or more of Sn, Ti and Zr, wherein in the framework structure of the zeolitic material according to (tt), the molar Al:Si ratio is in the range of from 0:1 to 0.001:1.

4. The process of any one of embodiments 1 to 3, wherein the feed stream F1 (feed_K1200) subjected to distillation according to (i) has a temperature in the range of from 40 to 160° C., preferably in the range of from 90 to 110° C.

5. The process of any one of embodiments 1 to 4, wherein at least 5 weight-%, preferably from 10 to 20 weight-% of the feed stream F1 (feed_K1200) consist of methylbut-3-en-1-ol, at least 30 weight-%, preferably from 40 to 50 weight-% of the feed stream F1 consist of the one or more solvents, at least 20 weight-%, preferably from 20 to 40 weight-% of the feed stream F1 consist of isobutene and at least 1 weight-%, preferably from 3 to 7 weight-% of the feed stream F1 consist of water, and wherein preferably at least 96 weight-%, more preferably from 97 to 99 weight-% of the feed stream F1 consist of 3-methylbut-3-en-1-ol, the one or more solvents, water and isobutene, in each case based on the total weight of the feed stream F1.

6. The process of embodiment 5, wherein the feed stream F1 further comprises one or more of 3-methylbutane-1,3-diol and an ester of formic acid and 3-methylbut-3-en-1-ol, wherein preferably at most 4 weight-%, more preferably at most 1 weight-% of the feed stream F1 consist of one or more of 3-methylbutane-1,3-diol and an ester of formic acid and 3-methylbut-3-en-1-ol.

7. The process of any one of embodiments 1 to 6, wherein at least 10 weight-%, preferably from 15 to 30 weight-% of the bottoms stream B1 (Su K1200) consist of methylbut-3-en-1 ol, at least 50 weight-%, preferably from 60 to 80 weight-% of the bottoms stream B1 (Su K1200) consist in the one or more solvents, at least 3 weight-%, preferably from 5 to 9 weight-% of the bottoms stream B1 (Su K1200) consist of water and less than 0.1 weight-%, preferably from 0.01 to 0.09 weight-% of the bottoms stream B1 consist of isobutene, and wherein preferably at least 96 weight-%, more preferably from 97 to 99 weight-% of the bottoms stream B1 consist of 3-methylbut-3-en-1-ol, the one or more solvents and water, in each case based on the total weight of the bottoms stream B1.

8. The process of any one of embodiments 1 to 7, wherein the one or more solvents comprised in the feed stream F1 have a boiling point higher than the boiling point of 3-methylbut-3-en-1-ol wherein the boiling point of 3-methylbut-3-en-1-ol is in the range of from 130 to 132° C. at an absolute pressure of 1 bar, wherein preferably the one or more solvents have a boiling point in the range of from 140° C. to 240° C. at an absolute pressure of 1 bar, more preferably in the range of from 160 to 200° C. at an absolute pressure of 1 bar.

9. The process of embodiment 8 wherein the one or more solvents is one or more of a mono-hydroxy alcohol, a poly-hydroxy alcohol and a ketone, wherein preferably the mono-hydroxy alcohol is a secondary or tertiary alcohol, wherein preferably the secondary and tertiary alcohol is one or more of 1-pentanol (138° C.), 2-hexanol (140° C.), 2-methyl-hexanol (142° C.), 4-methyl-hexanol (151° C.), 3-methyl-hexanol (152° C.), 3-ethylhexanol (159° C.), 4-heptanol (154° C.), 2-methyl-2-heptanol (157° C.), 3-heptanol (157° C.), 2-heptanol (158° C.), 3-Ethyl-3hexanol (159° C.), 3-methyl-2-heptanol (166° C.), 2-methyl-4-heptanol (166° C.), 4-ethyl-4-heptanol (179° C.), 2-octanol (180° C.), ethylhexanol (185° C.), more preferably the mono-hydroxy alcohol is 2-ethylhexanol, wherein preferably the poly-hydroxy alcohol is one or more of propanediol (187° C.), glycol (198° C.) and 1,4-butanediol (229° C.), and wherein preferably the ketone is one or more of cyclo-2-penten-1-on (153° C.), cyclohexanone (156° C.) and cycloheptanone (180° C.).

10. The process of embodiment 8 or 9 wherein the one or more solvent is 2-ethylhexanol.

11. The process of any one of embodiments 1 to 10, wherein the distillation unit according to (i) is a distillation tower, wherein the distillation according to (i) is carried out at a pressure at the top of the tower in the range of from 4 to 15 bar(abs), preferably in the range of from 7 to 13 bar(abs), and a temperature at the bottoms of the tower in the range of from 140 to 190° C., preferably in the range of from 170 to 180° C., wherein the tower preferably has from 5 to 40, more preferably from 15 to 25 theoretical plates.

12. The process of embodiment 11, wherein the distillation according to (i) is carried out at a temperature at the top of the tower in the range of from 40 to 80° C., preferably in the range of from 60 to 75° C.

13. The process of any one of embodiments 1 to 12, wherein the distillation unit according to (ii) is a distillation tower wherein the distillation according to (ii) is carried out at a pressure at the top of the tower in the range of from 0.1 to 2 bar(abs), preferably in the range of from 0.5 to 1.5 bar(abs), and a temperature at the bottoms of the tower in the range of from 130 to 180° C., preferably in the range of from 150 to 160° C., wherein the tower preferably has from 15 to 50, more preferably from 15 to 25 theoretical plates.
14. The process of embodiment 13, wherein the distillation according to (ii) is carried out at a temperature at the top of the tower in the range of from 60 to 110° C., preferably in the range of from 85 to 95° C.
15. The process of embodiment 13 or 14, further comprising separating a portion PT2 (Reflux_K1300) of the top stream T2 from T2 and feeding the portion PT2 back to the top of the distillation tower according to (i), wherein the portion PT2 is preferably in the range of from 60 to 95 weight-%, more preferably from 80 to 90 weight-% of the top stream T2, based on the total weight of the top stream T2.
16. The process of any one of embodiments 1 to 15, wherein the bottoms stream B2 (Su K1300) is enriched in methylbut-3-en-1-ol and in the one or more solvents relative to the bottoms stream B1 (Su K1200).
17. The process of any one of embodiments 1 to 16, wherein at least 10 weight-%, preferably from 20 to 35 weight-% of the bottoms stream B2 (Su K1300) consist of methylbut-3-en-1-ol, at least 55 weight-%, preferably from 70 to 90 weight-% of the bottoms stream B2 (Su K1300) consist of the one or more solvents, and less than 0.05 weight-%, preferably from 0.002 to 0.005 weight-% of the bottoms stream B2 (Su K1300) consist of water, and wherein preferably at least 96 weight-%, more preferably from 98 to 99 weight-% of the bottoms stream B2 consist of 3-methylbut-3-en-1-ol and the one or more solvents, in each case based on the total weight of the bottoms stream B2.
18. The process of any one of embodiments 1 to 17, wherein after (i) and prior to (ii), the process further comprises subjecting the bottoms stream B1 (Su K1200) to a vapor-liquid separation (B1300_Flash) in a phase separation unit, obtaining a liquid stream L7 (B1300_Fl) and a gas stream G7; (B1300_Gas) and subjecting the gas stream G7 and the liquid stream L7 to distillation according to (ii).
19. The process of embodiment 18, wherein the vapor-liquid separation (B1300_Flash) is carried out at a temperature in the range of from 90 to 140° C., preferably in the range of from 100 to 130° C., and at a pressure in the range of from 0.1 to 2 bar(abs), preferably in the range of from 0.5 to 1.5 bar(abs).
20. The process of any one of embodiments 1 to 19, wherein the distillation unit according to (iii) is a distillation tower, wherein the distillation according to (iii) is carried out at a pressure at the top of the tower in the range of from 0.03 to 1.5 bar(abs), preferably in the range of from 0.09 to 0.5 bar(abs), and a temperature at the bottoms of the tower in the range of from 90 to 150° C., preferably in the range of from 120 to 140° C., wherein the tower preferably has from 10 to 45, more preferably from 20 to 30 theoretical plates.
21. The process of any one of embodiments 1 to 20, wherein the distillation according to (iii) is carried out at a temperature at the top of the tower in the range of from 45 to 90° C., preferably in the range of from 65 to 75° C.
22. The process of any one of embodiments 1 to 21, wherein the top stream T3 (De K1500) is enriched in methylbut-3-en-1-ol relative to the bottoms stream B2 (Su K1300).
23. The process of any one of embodiments 1 to 22, wherein at least 97 weight-%, preferably from 99.5 to 99.95 weight-%, more preferably from 99.8 to 99.9 weight-% of the top stream T3 (De K1500) consist of 3-methylbut-3-en-1-ol, based on the total weight of the top stream T3 (De K1500).
24. The process of any one of embodiments 1 to 23, wherein the bottoms stream B3 (Su K1500) is enriched in the one or more solvents relative to the bottoms stream B2 (Su K1300).
25. The process of any one of embodiments 1 to 24, wherein at least 95 weight-%, preferably from 96 to 98 weight-% of the bottoms stream B3 (Su K1500) consist of the one or more solvents, (Su K1500), less than 1000 weight-ppm, preferably from 400 to 20 weight-ppm, more preferably from 200 to 50 weight-ppm of the bottoms stream B3 (Su K1500) consist of 3-methylbut-3-en-1-ol and wherein less than 100 weight-ppb, preferably from 50 to 0.1 weight-ppb of the bottoms stream B3 (Su K1500) consist of water, in each case based on the total weight of the bottoms stream B3, wherein more preferably, the bottoms stream B3 does not comprise water.
26. The process of any one of embodiments 1 to 25, wherein after (ii) and prior to (iii), the process further comprises subjecting the bottoms stream B2 (Su K1300) to a vapor-liquid separation (B1500) in a phase separation unit, obtaining an liquid stream L8 (B1500_Fl) and a gas stream G8 (B1500_Br), and subjecting the gas stream G8 and the liquid stream L8 to the distillation according to (iii).
27. The process of embodiment 26, wherein the vapor-liquid separation is carried out at a temperature in the range of from 80 to 120° C., preferably in the range of from 90 to 105° C., and at a pressure in the range of from 0.01 to 0.5 bar(abs), preferably in the range of from 0.08 to 0.2 bar(abs).
28. The process of any one of embodiments 1 to 27, wherein the top stream T2 (De K1300) additionally comprises 3-methylbut-3-en-1-ol, wherein preferably at least 30 weight-%, more preferably from 45 to 60 weight-% of the top stream T2 (De K1300) consist of methylbut-3-en-1-ol, and wherein at least 7 weight-%, preferably from 15 to 30 weight-% of the top stream T2 (De K1300) consist of water, less than 0.05 weight-%, preferably from 0.005 to 0.00001 weight-% of the top stream T2 consist of the one or more solvents, wherein preferably at least 60 weight-%, more preferably from 75 to 80 weight-% of the top stream T2 consist of 3-methylbut-3-en-1-ol and water, in each case based on the total weight of the top stream T2.
29. The process of any one of embodiments 1 to 28, wherein the process further comprises (iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq.
30. The process of embodiment 29, wherein the phase separation (B1310) of (iv) is carried out at a temperature in the range of from 20 to 60° C., preferably in the range of from 35 to 45° C., and at a pressure in the range of from 0.05 to 3 bar(abs), preferably in the range of from 0.5 to 1.5 bar(abs).
31. The process of embodiment 29 or 30 wherein at least 96 weight-%, preferably from 97 to 98.7 weight-% of the 3-methylbut-3-en-1-ol comprised in the top stream T2 is recovered in the organic liquid stream L2or.

32. The process of any one of embodiments 29 to 31, further comprising separating a portion PT2 (Reflux_K1300) and a portion L2or' (OP_Out) of the organic liquid stream L2or (B1310 OP) from the organic liquid stream L2or (B1310 OP) and feeding PT2 back to the top of the distillation tower according to (ii), wherein PT2 is preferably in the range of from 94 to 98 weight-%, preferably in the range of from 96 to 97 weight-% of L2or based in the total weight of L2or.

33. The process of any one of embodiments 29 to 32, wherein aqueous liquid stream L2aq (B 1310 WP) is enriched in water relative to the top stream T2 (De K1300).

34. The process of embodiment 32 or 33, wherein the process further comprises (iv-a) subjecting the portion L2or' (OP_Out) and the stream L2aq (B 1310 WP) to distillation (K1400) in a fourth distillation unit, obtaining a side stream S2 (DSA) comprising 3-methylbut-3-en-1-ol and water, wherein the side stream S2 (DSA) is preferably fed back to the distillation according to (ii) (K1300).

35. The process of embodiment 34, wherein the distillation unit according to (iv-a) is a distillation tower, wherein the distillation according to (iv-a) is carried out at a pressure at the top of the tower in the range of from 0.05 to 4 bar(abs), preferably in the range of from 0.5 to 1.5 bar(abs), and a temperature at the bottoms of the tower in the range of from 60 to 140° C., preferably in the range of from 90 to 110° C., wherein the tower preferably has from 7 to 40, more preferably 17 to 28 theoretical plates.

36. The process of embodiment 34 or 35, wherein the distillation according to (iv-a) is carried out at a temperature at the top of the tower in the range of from 40 to 95° C., preferably in the range of from 60 to 70° C.

37. The process of any one of embodiments 34 to 36, wherein the side stream S2 (DSA) has a temperature in the range of from 70 to 130° C., preferably in the range of from 95 to 100° C.

38. The process of any one of embodiments 34 to 37, wherein the side stream S2 (DSA) is enriched in methylbut-3-en-1-ol and water relative to the top stream T2 (De K1300).

39. The process of any one of embodiments 34 to 38, wherein at least 30 weight-%, preferably from 45 to 60 weight-% of the side stream S2 (DSA) consist of methylbut-3-en-1-ol, less than 70 weight-%, preferably from 40 to 55 weight-% of the side stream S2 (DSA) consist of water, and wherein preferably at least 97 weight-%, more preferably from 99 to 99.5 weight-% of the side stream S2 (DSA) consist of 3-methylbut-3-en-1-ol and water, in each case based on the total weight of the side stream S2 (DSA).

40. The process of any one of embodiments 34 to 37, wherein the side stream S2 (DSA) is recycled into the second distillation unit according to (ii).

41. The process of any one of embodiments 34 to 38, wherein after (iv-a), the process further comprises subjecting the side stream S2 (DSA) to heat exchange (W4120) in a heat exchange unit, obtaining a condensed stream C3 (Kond W1420) comprising 3-methylbut-3-en-1-ol and water; and subjecting the stream C3 (Kond W1420) to phase separation (B 1420) in a phase separation unit, obtaining an organic liquid stream L3or (B 1420_OP) comprising 3-methylbut-3-en-1-ol.

42. The process of embodiment 41, wherein the organic liquid stream L3or (B 1420_OP) is recycled to distillation according to (ii) (K1300).

43. The process of embodiment 41 or 42, wherein the phase separation (B1420) is carried out at a temperature in the range of from 65 to 140° C., preferably in the range of from 90 to 105° C., and at a pressure in the range of from 0.05 to 3 bar(abs), preferably in the range of from 0.5 to 1.5 bar(abs).

44. The process of any one of embodiments 41 to 42, wherein the organic liquid stream L3or (B 1420_OP) is enriched in 3-methylbut-3-en-1-ol relative to the top stream T2 (De K1300) and wherein at least 50 weight-%, preferably from 70 to 80 weight-% of the organic liquid stream L3or (B 1420_OP) consist of methylbut-3-en-1-ol, and less than 50 weight-%, preferably from 20 to 30 weight-% of the organic liquid stream L3or (B 1420_OP) consist of water, in each case based on the total weight of the organic liquid stream L3or (B 1420_OP).

45. The process of any one of embodiments 1 to 44, wherein the process further comprises recovering the one or more solvents comprised in the bottoms stream B3, (Su K1500) wherein the recovering preferably comprises
 (v) subjecting the bottoms stream B3 (Su K1500) to distillation (K1600) in a fifth distillation unit;
 (vi) recovering a side stream S5 (Si K1600) from the fifth distillation unit, comprising the one or more solvents.

46. The process of embodiment 45, wherein the distillation unit according to (v) comprises a distillation tower, preferably a Petlyuk distillation tower comprising a pre-fractionator tower and a main tower, more preferably a dividing wall tower.

47. The process of embodiment 46, wherein the distillation unit according to (v) is a Petlyuk distillation tower, wherein the distillation in the pre-fractionator tower is carried out at a pressure at the top of the tower in the range of from 0.005 to 1.5 bar(abs), preferably in the range of from 0.08 to 0.2 bar(abs) and a temperature at the bottoms of the tower in the range of from 100 to 135° C., preferably in the range of from 115 to 120° C., wherein the pre-fractionator tower preferably has from 7 to 45, more preferably 17 to 25 theoretical plates, and at a pressure at the top of the main distillation tower in the range of from 0.004 to 2 bar(abs), preferably in the range of from 0.08 to 0.2 bar(abs) and a temperature at the bottoms of the main distillation tower in the range of from 115 to 175° C., preferably in the range of from 135 to 155° C., wherein the main distillation tower preferably has from 12 to 75, more preferably 30 to 40 theoretical plates.

48. The process of embodiment 46, wherein the distillation unit according to (v) is a dividing wall distillation tower, wherein the distillation is carried out at a pressure at the top of the tower in the range of from 0.005 to 1.2 bar(abs), preferably in the range of from 0.07 to 0.2 bar(abs) and a temperature at the bottoms of the tower in the range of from 110 to 175° C., preferably in the range of from 130 to 155° C.

49. The process of any one of embodiments 45 to 47, wherein the side stream S5 (Si K1600) has a temperature in the range of from 100 to 140° C., preferably in the range of from 110 to 125° C.

50. The process of any one of embodiments 45 to 49, wherein the side stream S5 (Si K1600) is enriched in the one or more solvents relative to the bottoms stream B3 (Su K1500) and wherein at least 96 weight-%, preferably from 99.0 to 99.9 weight-% of the side stream S5 (Si K1600) consist of the one or more solvents, based on the total weight-% of the side stream S5.

51. The process of any one of embodiments 1 to 50, wherein at least 97 weight-%, preferably at least 99.5 weight-% of the 3-methylbut-3-en-1-ol comprised in F1 are recovered via T3, and wherein preferably at least 98 weight-%, more preferably at least 99.8 weight-% of the one or more solvents comprised in F1 are recovered via S5 (Si K1600).

52. The process of any one of embodiments 1 to 7, wherein the one or more solvents comprised in the feed stream F1 have a boiling point lower than the boiling point of 3-methylbut-3-en-1-ol wherein the boiling point of 3-methylbut-3-en-1-ol is in the range of from 130 to 132° C., wherein preferably the one or more solvents have a boiling point in the range of from 50 to 125° C., more preferably in the range of from 65 to 120° C., wherein the boiling points are at an absolute pressure of 1 bar.

53. The process of any one of embodiments 1 to 7 and 52 wherein the one or more solvents comprised in the feed stream F1 is one or more of a secondary alcohol, a tertiary alcohol a ketone, an ester and a nitrile
    wherein the secondary alcohol and the tertiary alcohol are preferably one or more of methanol (65° C.), ethanol (78° C.), tert-butanol (82° C.), 2-propanol (83° C.), 1-propanol (97° C.), 2-methyl-2-butanol (102° C.), isobutanol (108° C.), 3-pentanol (115° C.), 1-butanol (118° C.), 2-pentanol (119° C.), more preferably one or more of tert-butanol (82° C.), 2-propanol (83° C.), 2-methyl-2-butanol (102° C.), isobutanol (108° C.), 3-pentanol (115° C.), 1-butanol (118° C.) and 2-pentanol (119° C.) wherein
    the ketone is preferably one or more of acetone (56° C.), 2-butanon (80° C.) and 2-pentanon (102° C.), wherein the ester is preferably ethyl acetate (77° C.), wherein the nitrile is preferably acetonitrile.

54. The process of embodiment 52 or 53, wherein the distillation unit according to (i) is a distillation tower, wherein the distillation according to (i) is carried out at a pressure at the top of the tower in the range of from 4 to 20 bar(abs), preferably in the range of from 7 to 13 bar(abs), and a temperature at the bottoms of the tower in the range of from 130 to 180° C., preferably in the range of from 150 to 160° C., wherein the tower preferably has from 7 to 30, more preferably 15 to 20 theoretical plates.

55. The process of embodiment 54, wherein the distillation according to (i) is carried out at a temperature at the top of the tower in the range of from 40 to 90° C., preferably in the range of 60 to 70° C.

56. The process of any of embodiments 52 to 55, wherein the distillation unit according to (ii) is a distillation tower, wherein the distillation according to (ii) is carried out at a pressure at the top of the tower in the range of from 0.05 to 3 bar(abs), preferably in the range of from 0.5 to 1.5 bar(abs), and a temperature at the bottoms of the tower in the range of from 130 to 155° C., preferably in the range of from 130 to 140° C., wherein the tower preferably has from 10 to 50, more preferably 25 to 35 theoretical plates.

57. The process of any one of embodiments 52 to 56, wherein the distillation according to (ii) is carried out at a temperature at the top of the tower in the range of from 60 to 95° C., preferably in the range of from 75 to 85° C.

58. The process of any one of embodiments 52 to 57, wherein at least 84 weight-%, preferably from 93 to 95 weight-% of the bottoms stream B2 (Su K1300) consist of methylbut-3-en-1-ol, less than 0.25 weight-%, preferably from 0.01 to 0.1 weight-% of the bottoms stream B2 (Su K1300) consist of the one or more solvents, less than 0.3 weight-%, preferably from 0.01 to 0.1 weight-% of the bottoms stream B2 (Su K1300) consist of water, in each case based on the total weight of the bottoms stream B2.

59. The process of any one of embodiments 52 to 57, wherein after (i) and prior to (ii), the process further comprises subjecting the bottoms stream B1 (Su K1200) to a vapor-liquid separation (B1300_Flash) in a phase separation unit, obtaining an top stream T7 (B1300_Fl) and a bottoms stream B7 (B1300_Gas), and subjecting the bottoms stream B7 and the top stream T7 to distillation according to (ii).

60. The process of embodiment 59, wherein the phase separation (B1300_Flash) is carried out at a temperature in the range of from 80 to 150° C., preferably in the range of from 100 to 130° C., and at a pressure in the range of from 0.05 to 3 bar(abs), preferably in the range of from 0.5 to 1.5 bar(abs).

61. The process of any one of embodiments 54 to 60, wherein the distillation unit according to (iii) is a distillation tower, wherein the distillation according to (iii) is carried out at a pressure at the top of the tower in the range of from 0.03 to 1.4 bar(abs), preferably in the range of from 0.09 to 0.5 bar(abs), and at a temperature at the bottoms of the tower in the range of from 120 to 170° C., preferably in the range of from 140 to 150° C., wherein the tower preferably has from 4 to 25, more preferably from 7 to 12 theoretical plates.

62. The process of any one of embodiments 52 to 61, wherein the distillation according to (iii) (K1500) is carried out at a temperature at the top of the tower in the range of from 45 to 95° C., preferably in the range of from 65 to 75° C.

63. The process of any one of embodiments 21 to 62, wherein at least 98 weight-%, preferably from 99.5 to 99.95 weight-%, more preferably from 99.8 to 99.9 weight-% of the top stream T3 (De K1500) consist of 3-methylbut-3-en-1-ol and wherein less than 700 ppm (0.07 weight-%), preferably from 50 to 0.5 ppm (0.005 to 0.00005 weight-%), more preferably from 20 to 1 ppm (0.002 to 0.0001 weight-%) of the top stream T3 (De K1500) consist of the one or more solvents, in each case based on the total weight of the top stream T3.

64. The process of any one of embodiments 52 to 63, wherein after (ii) and prior to (iii), the process further comprises subjecting the bottoms stream B2 (Su K1300) to a vapor-liquid separation in a phase separation unit (B1500), obtaining gas stream G8 (B1500_Fl) and a liquid stream L8 (B1500_Br), and feeding back the liquid stream L8 and the gas stream G8 to the distillation unit according to (iii).

65. The process of embodiment 64, wherein the phase separation (B1500) is carried out at a temperature in the range of from 45 to 95° C., preferably in the range of from 70 to 80° C. and at a pressure in the range of from 0.005 to 0.8 bar(abs), preferably in the range of from 0.08 to 0.2 bar(abs).

66. The process of any one of embodiments 52 to 65, wherein the top stream T2 (De K1300) comprises water and the one or more solvents, wherein water and the one or more solvents optionally form an azeotrope.

67. The process of any one of embodiments 52 to 66, wherein at least 70 weight-%, preferably from 85 to 95 weight-% of the top stream T2 (De K1300) consist of the one or more solvents, at least 4 weight-%, preferably from 9 to 12 weight-% of the top stream T2 (De K1300) consist of water, and less than 2 weight-%, preferably from 0.5 to 0.05 weight-% of the top stream T2 (De K1300) consist of 3-methylbut-3-en-1-ol, in each case based on the total weight of the top stream T2.

68. The process of any one of embodiments 52 to 67, wherein at least 98 weight-%, preferably at least 99.5 weight-% of the 3-methylbut-3-en-1-ol comprised in F1 is recovered via T3.
69. The process of any one of embodiments 52 to 68, wherein at least 98 weight-%, preferably at least 99.6 weight-% of the one or more solvents comprised in F1 is recovered via T2.
70. The process of any one of embodiments 1 to 69, wherein at least 92 weight-%, preferably from 97 to 99.9 weight-%, more preferably 98 to 99.6 weight-% of the top stream T1 (Br K1200) consist of isobutene, based on the total weight of the top stream T1 (Br K1200).
71. The process of embodiment 70, wherein the top stream T1 has a temperature in the range of from 40 to 90° C., preferably in the range of from 60 to 70° C., and a pressure in the range of from 3 to 25 bar(abs), preferably in the range of from 7 to 13 bar(abs).
72. The process of any one of embodiments 1 to 70, comprising recovering (W1210) the isobutene, wherein the recovery preferably comprises subjecting the top stream T1 (Br K1200) to heat exchange in a heat exchange unit (W1210), obtaining a condensed stream C6 (Kond W 1215) comprising isobutene.
73. The process of any one of embodiments 1 to 72, further comprising separating a portion PT1 (Reflux_K1200) of the top stream T1 from T1 and feeding PT1 back to the top of the distillation tower according to (i), wherein PT1 is preferably in the range of from 20 to 75 weight-%, more preferably in the range of from 40 to 50 weight-% of T1 based in the total weight of T1.
74. The process of any one of embodiments 1 to 73, further comprising separating a portion PT1 (Reflux_K1200) of the condensed stream C6 and feeding PT1 back to the top of the distillation tower according to (i), wherein PT1 is preferably in the range of from 20 to 75 weight-%, more preferably in the range of from 40 to 50 weight-% of the condensed stream C6, based in the total weight of C6.
75. The process of any one of embodiments 1 to 74, wherein at least 97 weight-%, preferably at least 99.6 weight-% of the isobutene comprised in F1 is recovered via T1.
76. The process of any one of embodiments 1 to 75, wherein the one or more solvents is a mixture of tert-butanol and methanol.
77. The process of embodiment 76, wherein the top stream T2 is an azeotropic mixture comprising from 75 to 95 weight-% tert-butanol, from 0.05 to 2 weight-% methanol and from 3 to 15 weight-% water, preferably 88 to 92 weight-% tert-butanol, 0.2 to 0.8 weight-% methanol and 8 to 11 weight-% water.
78. The process of embodiment 77, wherein the process further comprises subjecting the top stream T2 to azeotropic distillation.
79. The process of any one of embodiments 1 to 78, wherein prior to (i) the process comprises
    (t) providing a mixture comprising formaldehyde, isobutene and the one or more solvents;
    (tt) contacting the mixture provided in (t) with a condensation catalyst comprising, preferably consisting of an heterogeneous catalyst and obtaining the feed stream F1;
80. The process of embodiment 79, wherein the heterogeneous catalyst comprises, preferably consists, of a Lewis acid catalyst, wherein preferably the Lewis acid catalyst is a zeolitic material, a mesoporous silica, a metal oxide or mixed metal oxides supported rare earth metals and combination of two or more thereof.
81. The process of embodiment 79, wherein the zeolitic material is a zeolitic material as defined in embodiment 2, a metal doped zeolites, preferably a rare-earth metal doped zeolites or a alkaline earth modified Al-containing zeolites, preferably the zeolitic material is as defined in embodiment 2.
82. The process of embodiment 79, wherein the mesoporous silica is a Sn mesoporous silica
83. The process of embodiment 79, wherein the metal oxide is silica, alumina, clays, TiO2, ZnO, $ZNO_2$.
84. The process of embodiment 79 wherein the rare-earth metal is one or more of Ce, Y, La, and preferably wherein the support is one or more of alumina, silica and a polymeric support-
85. A composition comprising 3-methylbut-3-en-1-ol, wherein at least 99 weight-%, preferably from 99.5 to 99.99 weight-%, more preferably from 99.8 to 99.9 weight-% of said composition consist of 3-methylbut-3-en-1-ol, obtainable or obtained as top stream T3 by a process according to any one of embodiments 1 to 84.
86. Use of the composition according to embodiment 85 as a starting material for preparing a monomeric, oligomeric or polymeric compound, preferably as a starting material for preparing a monomeric, oligomeric or polymeric compound, preferably as a starting material for preparing an aroma chemical, preferably one or more of 3,7-dimethyl-2,6-octadienal (Citral), 2-isobutyl-4-hydroxy-4-methyl tetrahydropyran (Pyranol), or as a starting material for preparing an isoprenol polyether derivative as a component of a copolymer which is suitable as a superplasticizer for a hydraulic binder.

The invention is further illustrated by the following reference examples and examples.

EXAMPLES

Reference Example 1: Preparation of MBE

Reference Example 1.1: Preparation of a Zeolitic Material Having Framework Type BEA and Comprising Sn (Sn-BEA)

a) Preparation of Sn-BEA-Zeolite
Materials used:

| 50 g | Deboronated BEA-zeolite, spray-dried (prepared according to Example 1 (ii) of WO 2014/060259 A |
| 14.2 g | Sn(OAc)$_2$ (tin(II)acetate) from Aldrich |

50 g of deboronated BEA zeolite and 14.2 g Sn(OAc)$_2$ were combined in the laboratory mixer and were ground for 15 min. The obtained mixture was then calcined in a muffle furnace by raising the temperature at the rate of 2 K/min to 500° C. for 3 h. 55.5 g of the zeolite of a) were obtained.

b) Acid Treatment
Materials used:

| 55 g | Sn-BEA zeolite according to a) |
| 1650 g | HNO$_3$ 30 weight- % aqueous solution |

761.5 g of a solution of 65% HNO$_3$ were added to a stirred 2 L vessel charged with 888.5 g of deionized water. Under continuous stirring, 55 g of the zeolite according to a) were added to the mixture. The obtained suspension was heated to 100° C. and refluxed for 20 h. The suspension was then cooled, filtered and washed with distilled water until neutral pH (<100 microsiemens). The filtered zeolite was then calcined in the muffle furnace by raising the temperature at the rate of 3 K/min to 120° C. for 10 h followed by raising the temperature at the rate of 2 K/min to 550° C. for 10 h. 52.8 g of the zeolite of b) were obtained.

c) Preparation of a Molding
Materials used:

| | |
|---|---|
| 60 g | Sn-BEA zeolite of b) |
| 17.37 g | ZrOH(OAc)$_3$ (~10% ZrO$_2$) from Aldrich |
| 3 g | Walocel ® Wolf Walsrode AG PUFAS Werk KG |
| 53 mL | DI water |

60 g of Sn-BEA zeolite of b), 17.37 g of ZrOH(OAc)$_3$ and 3 g of Walocel® were combined and mixed in a kneader. 53 mL of deionized water were then added to the mixture which was kneaded until combined. The total kneading time was 30 min. The obtained zeolite was then calcined in the muffle furnace by raising the temperature at the rate of 3 K/min to 120° C. for 6 h followed by raising the temperature at the rate of 2 K/min to 550° C. for 5 h under air. 52.8 g of the molding with a bulk density of 440 g/L were obtained.

Reference Example 1.2: Synthesis of MBE in the High Boiling Solvent 2-ethylhexanol 55 g of an aqueous solution of formaldehyde (FA) (49 weight-%) were dissolved in 445 g of 2-ethylhexanol. A formaldehyde solution (5.39 weight-%) was obtained. This solution was dosed to an isothermal tubular reactor at 32 g/h (0.05 mol FA/h). The isobutene flask was pressurized with helium (to liquefy the gas) and pumped into the reactor at 31.3 g/h (0.55 mol/h). The two streams were pressurized to 20 bar(abs) and tempered to 100° C. before entering the reactor. The tubular reactor had a length of 110 cm and contained 10.85 g of a Sn-BEA catalyst. The reactor was operated at 100° C. and at a constant pressure of 20 bar(abs). The residence time was of about 15.67 min. The reaction was run for 48 h. The reaction mixture which was obtained was fed as stream F1 according to the invention to the inventive work-up process. In the following, this specific feed stream is denoted as Feed_K1200. The composition of the Feed_K1200 is given in Table 1 below.

Reference Example 1.3: Synthesis of MBE in a Low Boiling Solvent 55 g of an aqueous solution of formaldehyde (FA) (49 weight-%) were dissolved in 445 g of tert-butanol. A formaldehyde solution (5.39 weight-%) was obtained. This solution was dosed to an isothermal tubular reactor at 32 g/h (0.05 mol FA/h). The isobutene flask was pressurized with helium (to liquefy the gas) and pumped into the reactor at 31.3 g/h (0.55 mol/h). The two streams were pressurized to 20 bar(abs) and tempered to 100° C. before entering the reactor. The tubular reactor had a length of 110 cm and contained 10.85 g of a Sn-BEA catalyst according to Reference Example 1.1. The reactor was operated at 100° C. and at a constant pressure of 20 bar(abs). The residence time was of about 15.67 min. The reaction was run for 48 h. The reaction mixture which was obtained was fed as stream F1 according to the invention to the inventive work-up process. In the following, this specific feed stream is denoted as Feed_K1200. The composition of the Feed_K1200 is given in Table 2 below.

Example 1: MBE Recovery from the High Boiling Solvent 2-Ethlyhexanol (FIG. 1)

The following explains a series of steps of the reaction in accordance with the present invention. The streams and the apparatus are identified according to the abbreviation used in FIG. 1.

a) Distillation of the feed stream Feed_K1200 (F1) (first distillation unit)

The reaction mixture of Reference Example 1 Feed-K1200 (F1) was fed at a temperature of 100° C. and at a mass flow rate of 7.5×10$^{-4}$ kg/h to a 20-plate distillation tower K1200. The feed was fed at plate 18 of the distillation tower K1200. The distillation was carried out at a top pressure of 9 bar(abs) and a top temperature of 68.7° C. and at a bottoms temperature of 174.0° C. A bottoms stream Su_K1200 (B1) and a top stream Br_K1200 (T1) were withdrawn. The respective compositions are disclosed in Table 1 herein below.

b) Distillation of the bottoms stream Su_K1200 (B1) (second distillation unit)

The bottoms stream Su_K1200 (B1) of a) was subjected to phase separation in a flash drum unit at a mass flow rate of 4.8×10$^4$ kg/h, at a temperature of 117° C. and a pressure of 1 bar(abs). A liquid stream B1300_F1 (L7) and a gas stream B1300_G (G7) were obtained. The liquid stream B1300_F1 (L7) and the gas stream B1300G (G7) were fed into a 35 plate distillation tower K1300 operating at a top pressure of 1 bar(abs) and a top temperature of 91° C. and at a bottoms temperature of 144° C. The liquid stream B1300_F1 (L7) was feed at plate 20 at a mass flow rate of 4.1×10$^4$ kg/h and the gas stream B1300_G (G7) was fed at plate 20 at a mass flow rate of 6.2×10$^3$ kg/h. A top stream De K1300 (T2) and a bottoms stream Su_K1300 (T3) were withdrawn from the distillation tower K1300. The respective compositions are disclosed in Table 1 herein below.

c) Distillation K1500 of bottoms stream (B2) Su_K1300 (third distillation unit)

The bottoms stream Su_K1300 (B2) from b) was fed into a phase separation unit (flash drum) B1500 at a mass flow rate of 4.4×10$^4$ kg/h. The phase separation unit was operated at a temperature of 102° C. and a pressure of 0.1 bar(abs). A liquid stream B1500_F1 (L8) and a gas stream B1500_Br (G8) were withdrawn. The liquid stream and the gas stream were fed into a 25 plate distillation tower K1500 operating at a top pressure of 0.1 bar(abs), at a top temperature of 73° C. and at a bottoms temperature of 118.5° C. The liquid stream B1500_F1 (L8) and the gas stream B1500_Br (G8) were fed at plate 15 and plate 16 respectively at a respective mass flow rate of 3.0×10$^4$ kg/h and 1.4×10$^4$ kg/h. A top stream De K1500 (T3) and a bottoms stream Su_K1300 (B3) were withdrawn. The top stream De K1500 (T3) consisted of about 100 weight-% of MBE. The compositions of the streams are disclosed in details in Table 1 herein below.

d) Recycling of top stream De K1300 (T3) (fourth distillation unit)

The top stream De K1300 (T3) of b) was fed into a phase separation unit B1310 at a mass flow rate of 3.8×10$^4$ kg/h. The phase separation unit was operated at a pressure of 1 bar(abs) and a temperature of 40° C. Two streams B1310_WP (L2aq) and B1310_OP (L2) were obtained. B1310_WP (L2aq) was fed directly at a mass flow rate of $4.1 \times 10^3$ into a 22 plate distillation column K1400 at plate 12. Stream B1310_OP was split into a reflux stream Reflux_K1300 (PT2) that was fed at a mass flow rate of $3.3 \times 10^4$ kg/h to the top of the distillation tower K1300 of c) and into a stream OP_out that was fed at plate 12 and at a mass flow rate of $3.9 \times 10^2$ kg/h into the 22 plate distillation column K1400. The distillation tower K1400 was operating at a top pressure of 1 bar(abs), at a top temperature of 65° C. and at a bottoms temperature of 99.5° C. Three streams were withdrawn. The top stream De K1400 comprising low boilers (waste) and the bottoms stream Su_K1400 were discharged. The side stream DSA (S2) was withdrawn at plate 6. The side stream DSA having a temperature of 95.9° C. was fed at a mass flow rate $1.3 \times 10^{-3}$ into a heat exchanger W1420 operating at a pressure of 1 bar(abs). Two streams were recovered: the condensed stream Kond_W1420 (C3) and the gas stream Abg_W1420. The gas stream was discharged. The liquid stream Kond_W1420 (C3) was fed into a phase separation unit B1420 operating at a pressure of 1 bar(abs) and a temperature of 95.7° C. A liquid stream B1420_OP (L3) and a liquid stream B1420_WP were obtained. The liquid stream B1420_OP (L3) was fed back into distillation tower K1300 of c) at plate 17 and at a mass flow rate of $6.4 \times 10^2$ kg/h. The gas stream B1420_WP was fed back into the distillation tower K1400 at plate 12 and at a mass flow rate of $6.9 \times 10^2$ kg/h. The compositions of the streams are reported in Table 1 herein below.

e) Recovery of the high boiling solvent 2-ethylhexanol (2-EH): Distillation of bottoms stream Su_K1500 (B3) (fifth distillation unit)

The bottoms stream Su_K1500 (B3) obtained from above c) was subjected to a two distillation towers distillation. Su_K1500 (B3) was fed into a 20 plate-pre-column K1600_VK at plate 10 and at a mass flow rate of $3.4 \times 10^4$ kg/h. K1600_VK was operating at a top pressure of 1 bar(abs), a top temperature of 118.1° C. and at a bottoms temperature of 118.5° C. A liquid stream APP10_Lu was withdrawn from plate 1 of K1600_VK and fed into the distillation tower K1600 at plate 10 and at a mass flow rate of $4.8 \times 10^4$ kg/h. A gas stream APP10_GO was withdrawn from plate 20 of K1600_VK and fed at plate 10 into the 40-plate distillation tower K160_HK at a mass flow rate of $3.2 \times 10^2$ kg/h. The distillation tower K1600 HK was operating at a top pressure of 0.1 bar(abs), at a top temperature of 97.5° C. and at a bottoms temperature of 146.5° C. From the distillation tower K1600 the following streams were withdrawn:

Liquid stream APP10_LO was withdrawn from plate 31 and fed back to the pre-column K1600_VK at plate 20 and at a mass flow rate of $1.5 \times 10^2$ kg/h; Gas stream APP10_Gu was withdrawn from plate 10 and fed back to the pre-column K1600_VK at plate 1 at a mass flow rate of $3.1 \times 10^2$ kg/h; liquid stream Su_K1600 was withdrawn from the bottoms (evaporator) and discharged; stream De K1600 was withdrawn from the bottoms and discharged and liquid side stream Si_K1600 (S5) was withdrawn from plate 21. The compositions of the streams are disclosed in Table 1 herein below.

f) Recovery of isobutene from top stream Br_K1200 (T1)

Top stream Br_K1200 (T1) having a temperature of 68.6° C. was withdrawn from the top of the distillation tower K1200 of a) and fed at a mass flow rate of $3.7 \times 10^4$ kg/h into the heat exchanger W1210 operating at a pressure of 9 bar(abs). A liquid stream Kond_W1210 and a gas stream Abg W1210 were obtained. The gas stream Abg W1210 as discharged. The liquid stream Kond_W1210 was fed into W1215 a condenser operating at a temperature of 40° C. at a mass flow rate of $3.7 \times 10^4$ kg/h. Two streams were obtained: a reflux stream reflux_K1200 which was fed back into distillation tower K1200 at plate 20 and at a mass flow rate of $1.0 \times 10^2$ kg/h and a stream Out_W1215 comprising 99.6 weight-% of isobutene which was recovered.

TABLE 1

Compositions of the streams in weight-%, if not indicated as ppb

| | Feed_K1200 F1 | Reflux_K1200 | Su_K1200 B1 | Br_K1200 T1 | Kond_W1210 | Abg_W1200 | Out_W1215 |
|---|---|---|---|---|---|---|---|
| | Mass flow rate/(kg/h) | | | | | | |
| MBE | 13.8 | 0.0038 | 21.6 | 0.0038 | 0.0038 | 292 ppb | 0.0038 |
| Isobutene | 36.0 | 99.6 | 0.0500 | 99.6 | 99.6 | 99.4 | 99.6 |
| 2-EH | 44.0 | 218 ppb | 68.8 | 218 ppb | 218 ppb | 0 ppb | 218 ppb |
| H2O | 4.8 | 0.0563 | 7.5 | 0.0563 | 0.0563 | 0.0016 | 0.0563 |
| MBE-Formate | 0.2 | 0.0002 | 0.3 | 0.0002 | 0.0002 | 27 ppb | 0.0002 |
| MP-1,3-Diol | 0.9 | 0 ppb | 1.5 | 0 ppb | 0 ppb | 0 ppb | 0 ppb |
| MeOH | 0.3 | 0.3 | 0.2 | 0.3 | 0.3 | 0.6 | 0.3 |
| T_BuOH | 0.1 | 0.0365 | 0.2 | 0.0365 | 0.0365 | 0.0071 | 0.0365 |
| Total in kg/h | $7.506 \times 10^4$ | $1.000 \times 10^4$ | $4.797 \times 10^4$ | $3.709 \times 10^4$ | $3.709 \times 10^4$ | 1.000 | $2.709 \times 10^4$ |

| | B1300_FI L7 | B1300_Gas G7 | B1420_OP | Reflux_K1300 | Su_K1300 B2 | De_K1300 T2 | B1310_WP L2aq | B1310_OP L2op | Op_out |
|---|---|---|---|---|---|---|---|---|---|
| | Mass flow rate / (kg/h) | | | | | | | | |
| MBE | 19.4 | 34.7 | 74.6 | 56.3 | 23.5 | 50.7 | 6.2 | 56.3 | 56.3 |
| Isobutene | 0.0051 | 0.3 | 184 ppb | 0.3 | — | 0.3 | 0.5 | 0.3 | 0.3 |
| 2-EH | 76.5 | 22.6 | — | — | 74.9 | 0 ppb | — | — | — |
| H2O | 2.1 | 39.9 | 24.3 | 12.3 | — | 20.8 | 88.4 | 12.3 | 12.3 |
| MBE-Formate | 0.2 | 0.6 | 1.0 | 24.8 | 0.0050 | 22.2 | 1.0 | 24.8 | 24.8 |

TABLE 1-continued

Compositions of the streams in weight-%, if not indicated as ppb

|  |  |  |  |  |  |  |  |  |  |
|---|---|---|---|---|---|---|---|---|---|
| MP-1,3-Diol | 1.7 | 0.1 | — | — | 1.6 | — | — | — | — |
| MeOH | 0.0637 | 1.1 | 0.0626 | 1.9 | — | 1.9 | 2.3 | 1.9 | 1.9 |
| T_BuOH | 0.0734 | 0.7 | 0.0041 | 4.5 | — | 4.1 | 1.5 | 4.5 | 4.5 |
| Total in kg/h | $4.115*10^4$ | $6.818*10^3$ | $6.414*10^3$ | $3.300*10^4$ | $4.404*10^4$ | $3.357*10^4$ | $4.176*10^3$ | $3.339*10^4$ | $3.943*10^2$ |

|  | B1500_FI L8 | B1500_Br G8 | B1500_Br G8 | Su_K1500 B3 | De_K1500 T3 | App10_LO | App10_GU |
|---|---|---|---|---|---|---|---|
|  | Mass flow rate/(kg/h) | | | | | | |
| MBE | 11.4 | 50.1 | 50.1 | 0.0050 | 100.0 | 0.0005 | 0 ppb |
| Isobutene | — | — | — | — | — | — | — |
| 2-EH | 86.5 | 49.6 | 49.6 | 97.9 | 0.0010 | 100.0 | 99.4 |
| H2O | — | — | — | — | — | — | — |
| MBE-Formate | 0.0021 | 0.0114 | 0.0114 | 1 ppb | 0.0213 | 0 ppb | — |
| MP-1,3-Diol | 2.2 | 0.3 | 0.3 | 2.1 | 0 ppb | 0.0006 | 0.6 |
| MeOH | — | — | — | — | — | — | — |
| T_BuOH | — | — | — | — | — | — | — |
| Total in kg/h | $3.029*10^4$ | $1.375*10^4$ | $1.375*10^4$ | $3.370*10^4$ | $1.034*10^4$ | $1.462*10^4$ | $3.163*10^4$ |

|  | App10_Lu | App10_GO | Su_K1600 | De_K1600 | SI_K1600 | B1420_WP | Su_K1400 |
|---|---|---|---|---|---|---|---|
|  | Mass flow rate / (kg/h) | | | | | | |
| MBE | 0 ppb | 0.0055 | — | 16.9 | 0 ppb | 17.6 | 0.0286 |
| Isobutene | — | — | — | — | — | 273 ppb | 0 ppb |
| 2-EH | 98.2 | 100.0 | 0.1 | 83.1 | 100.0 | — | — |
| H2O | — | — | — | — | — | 82.2 | 100.0 |
| MBE-Formate | 0 ppb | 1 ppb | — | 0.0004 | — | 0.0686 | 0 ppb |
| MP-1,3-Diol | 1.8 | 0.0010 | 99.9 | 0 ppb | 0.0010 | — | — |
| MeOH | — | — | — | — | — | 0.0637 | 70 ppb |
| T_BuOH | — | — | — | — | — | 0.0016 | 0 ppb |
| Total in kg/h | $4.827*10^4$ | $3.169*10^4$ | $7.004*10^2$ | $1.000*10^1$ | $3.299*10^4$ | $6.943*10^2$ | $3.493*10^3$ |

|  | De_K1400- | DSA_S2 | Kond_W1420 | Abg_W1420 |
|---|---|---|---|---|
|  | Mass flow rate/(kg/h) | | | |
| MBE | 0.3 | 45.0 | 45.0 | 43.7 |
| Isobutene | 5.5 | 231 ppb | 230 ppb | 0.0002 |
| 2-EH | — | — | — | — |
| H2O | 21.1 | 54.4 | 54.4 | 53.3 |
| MBE-Formate | 31.0 | 0.5 | 0.5 | 2.8 |
| MP-1,3-Diol | — | — | — | — |
| MeOH | 23.8 | 0.0633 | 0.0632 | 0.2 |
| T_BuOH | 18.2 | 0.0028 | 0.0028 | 0.0151 |
| Total in kg/h | $3.339*10^2$ | $1.337*10^3$ | $1.337*10^3$ | 1.000 |

In Table 1, MBE stands for 3-methylbut-3-en-1-ol, 2-EH stands for 2-ethylhexanol, MP-1,3-Diol stands for 3-methylbutane-1,3-diol, MBE-Formiate stands for the ester of formic acid and 3-methylbut-3-en-1-ol and T_BuOH stands for tert-butanol.

Example 2: MBE Recovery from the Low Boiling Solvent Tert-Buthanol (FIG. 2)

The following explains a series of steps of the reaction in accordance with the present invention. The streams and the apparatus are identified according to the abbreviations used in FIG. 2 and the Reference Example 1.3.

a) Distillation of the feed stream Feed_K1200 (F1) (first distillation unit)

The reaction mixture of Reference Example 1 (Feed-K1200) was fed at a temperature of 100° C. and at a mass flow rate of $7.5 \times 10^4$ kg/h to a 16-plate distillation tower K1200. The feed was fed at plate 12 of the distillation tower K1200. The distillation was carried out at a top pressure of 9 bar(abs), at a top temperature of 66.6° C. and at a bottoms temperature of 151.4° C. A bottoms stream Su_K1200 (B1) and a top stream Br_K1200 (T1) were withdrawn. The respective compositions are disclosed in Table 2 herein below.

b) Distillation of bottoms stream Su_K1200 (B1) (second distillation unit)

The bottoms stream Su_K1200 (B1) was subjected to phase separation in a flash separator at a mass flow rate of $4.8 \times 10^4$ kg/h, at a temperature of 85.5° C. and a pressure of 1 bar(abs). A liquid stream B1300_F1 (L7) and a gas stream B1300_G (G7) were obtained. The liquid stream B1300F1 and the gas stream B1300_G were fed into a 30 plate distillation tower operating at a top pressure of 1 bar(abs) and a top temperature of 79° C. and at a bottoms temperature of 130.5° C. The liquid stream B1300_F1 (L7) was feed at plate 17 at a mass flow rate of $3.1 \times 10^4$ kg/h and the gas stream B1300_G (G7) was fed at plate 18 at a mass flow rate of $1.7 \times 10^4$ kg/h. A top stream De K1300 (T2) and a bottoms stream Su_K1300 (B2) were withdrawn from the distillation tower. The respective compositions are disclosed in Table 2 herein below.

c) Distillation K1500 of bottoms stream (B2) Su_K1300 (third distillation unit)

The bottoms stream Su_K1300 (B2) from b) was fed into a phase separation unit at a mass flowrate of $3.1 \times 10^4$ kg/h. The phase separation unit flash was operating at a temperature of 74° C. and a pressure of 0.1 bar(abs). A liquid stream B1500_F1 (L8) and a gas stream B1500_Br (G8) were obtained. The liquid stream and the gas stream were fed into a 10 plate distillation tower operating at a top pressure of 0.1 bar(abs), at a top temperature of 73° C. and at a bottoms temperature of 146.5° C. The liquid stream B1500_F1 and the gas stream B1500_Br were fed a plate 5 and plate 6 respectively at a respective mass flow rate of $7.7 \times 10^3$ kg/h and $3.3 \times 10^3$ kg/h. A top stream De K1500 (T3) and a bottoms stream Su_K1500 (B3) were withdrawn. The respective compositions are disclosed in Table 2 herein below.

d) Recovery of isobutene from top stream Br_K1200 (T1)

The top stream Br_K1200 (T1) was withdrawn from the top of the distillation tower K1200 of a) and fed at a mass flow rate of $4.9 \times 10^4$ kg/h into the heat exchanger W1210 operating at a pressure of 9 bar(abs) and at a temperature of 66° C. A liquid stream Kond_W1210 and a gas stream Abg_W1210 were obtained. The gas stream Abg W1210 as discharged. The liquid stream Kond_W1210 was fed into the condenser W1215 operating at a temperature of 40° C. at a mass flow rate of $4.9 \times 10^4$ kg/h. Two streams were obtained: a reflux stream reflux_K1200 (PT1) which was fed back into distillation tower K1200 at plate 16 and at a mass flow rate of $2.2 \times 10^4$ kg/h and a stream Out_W1215 comprising 99.6 weight-% of isobutene which was recovered The respective compositions are disclosed in Table 2 herein below.

TABLE 2

| Compositions of the streams in weight-% | | | | | | |
|---|---|---|---|---|---|---|
| | Feed_K1200 | Reflux_K1200 | Su_K1200 | Br_K1200 | Kond_W1210 | Abg_W1200 |
| | Mass flow rate/(kg/h) | | | | | |
| MBE | 13.8 | 1 ppb | 21.6 | 1 ppb | 1 ppb | 0 ppb |
| Isobutene | 36.0 | 99.6 | 0.0500 | 99.6 | 99.6 | 99.7 |
| H2O | 4.8 | 741 ppb | 7.5 | 741 ppb | 741 ppb | 22 ppb |
| MBE-Formiate | 0.2 | 0 ppb | 0.3 | 0 ppb | 0 ppb | 0 ppb |
| MP-1,3-Doil | 0.9 | — | 1.5 | — | — | — |
| MeOH | 0.3 | 0.2 | 0.3 | 0.2 | 0.2 | 0.3 |
| T_BuOH | 44.0 | 0.3 | 68.8 | 0.3 | 0.3 | 0.0531 |
| Total in kg/h | $7.497 \times 10^4$ | $2.158 \times 10^4$ | $4.788 \times 10^4$ | $4.867 \times 10^4$ | $4.8679 \times 10^4$ | 1.000 |

| | Out_W1215 | B1300_FI | B1300_gas | Su_K1300 | De_K1300 | B1500_FI |
|---|---|---|---|---|---|---|
| | Mass flow rate/(kg/h) | | | | | |
| MBE | 1 ppb | 30.1 | 6.2 | 93.6 | 0.0500 | 90.9 |
| Isobutene | 99.6 | 0.0066 | 0.1 | — | 0.0650 | — |
| H2O | 741 ppb | 6.2 | 9.9 | 0 ppb | 9.8 | — |
| MBE-Formiate | 0 ppb | 0.4 | 0.1 | 0.0500 | 0.4 | 0.0368 |
| MP-1,3-Doil | — | 2.3 | 0.0075 | 6.3 | — | 9.0 |

TABLE 2-continued

| Compositions of the streams in weight-% | | | | | |
|---|---|---|---|---|---|
| MeOH | 0.2 | 0.3 | 0.4 | — | 0.4 | — |
| T_BuOH | 0.3 | 60.8 | 83.2 | 0 ppb | 89.3 | 0 ppb |
| Total in kg/h | $2.709*10^4$ | $3.081*10^4$ | $1.707*10^3$ | $1.103*10^4$ | $3.685*10^4$ | $7.682*10^3$ |

| | B1500_Br | Su_K1500 | De_K1500 |
|---|---|---|---|
| | Mass flow rate/(kg/h) | | |
| MBE | 99.8 | 349 ppb | 99.9 |
| Isobutene | — | — | — |
| H2O | — | — | — |
| MBE-Formiate | 0.0803 | 0 ppb | 0.0534 |
| MP-1,3-Doil | 0.2 | 100.0 | 0.0001 |
| MeOH | — | — | — |
| T_BuOH | 0 ppb | — | 0 ppb |
| Total in kg/h | $3.345*10^3$ | $7.000*10^2$ | $1.033*10^4$ |

In Table 2, MBE stands for 3-methylbut-3-en-1-ol, 2-EH stands for 2-ethylhexanol, MP-1,3-Diol stands for 3-methylbutane-1,3-diol, MBE-Formiate stands for the ester of formic acid and 3-methylbut-3-en-1-ol and T_BuOH stands for tert-butanol.

CITED PRIOR ART

Figure 1:
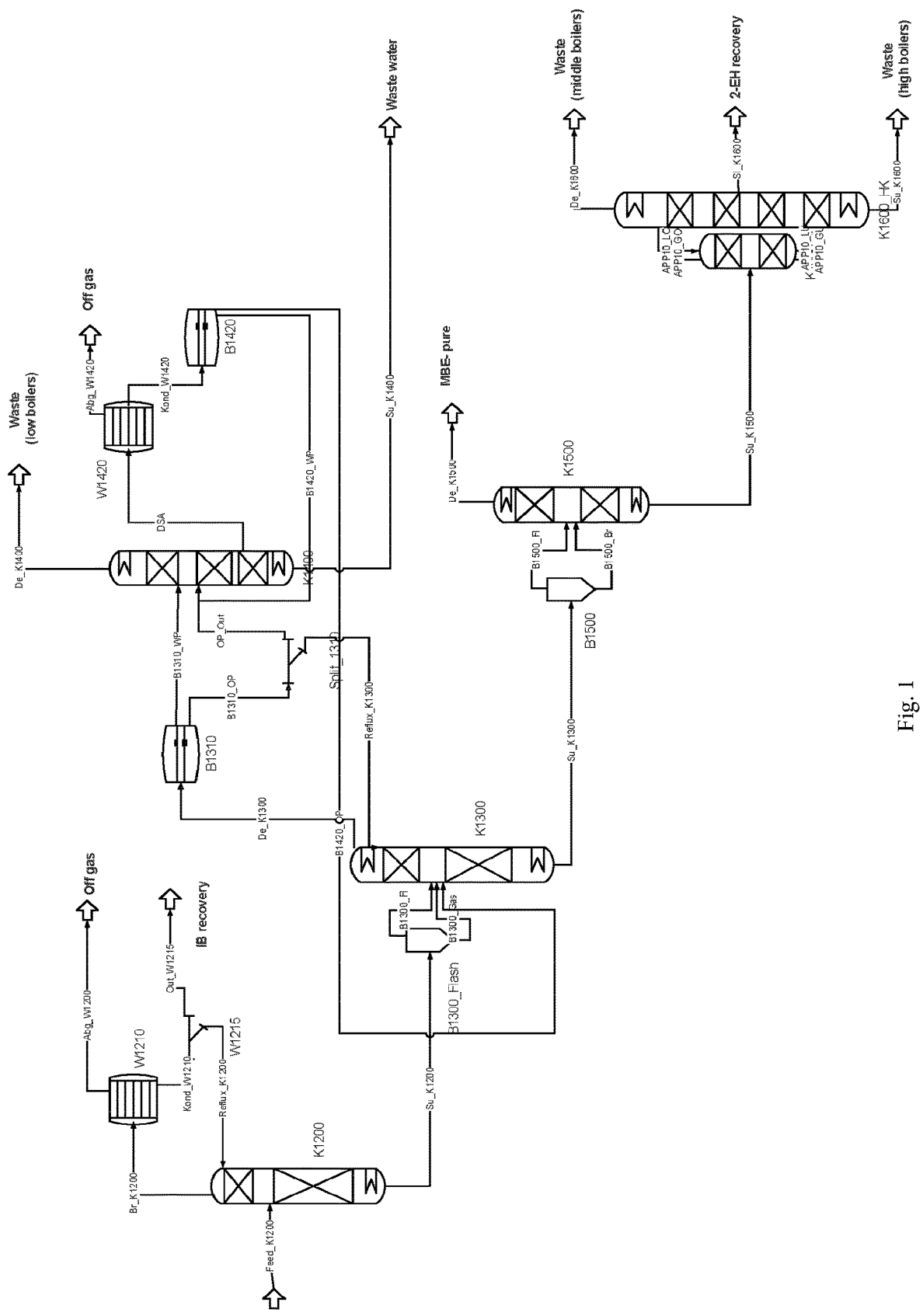
FIG. 1: shows the scheme of the process according to example 1: the MBE recovery from the high boiling solvent 2-ethlyhexanol, the recovery of isobutene and the recovery of high boiling solvent 2-ethlyhexanol
Figure 2:
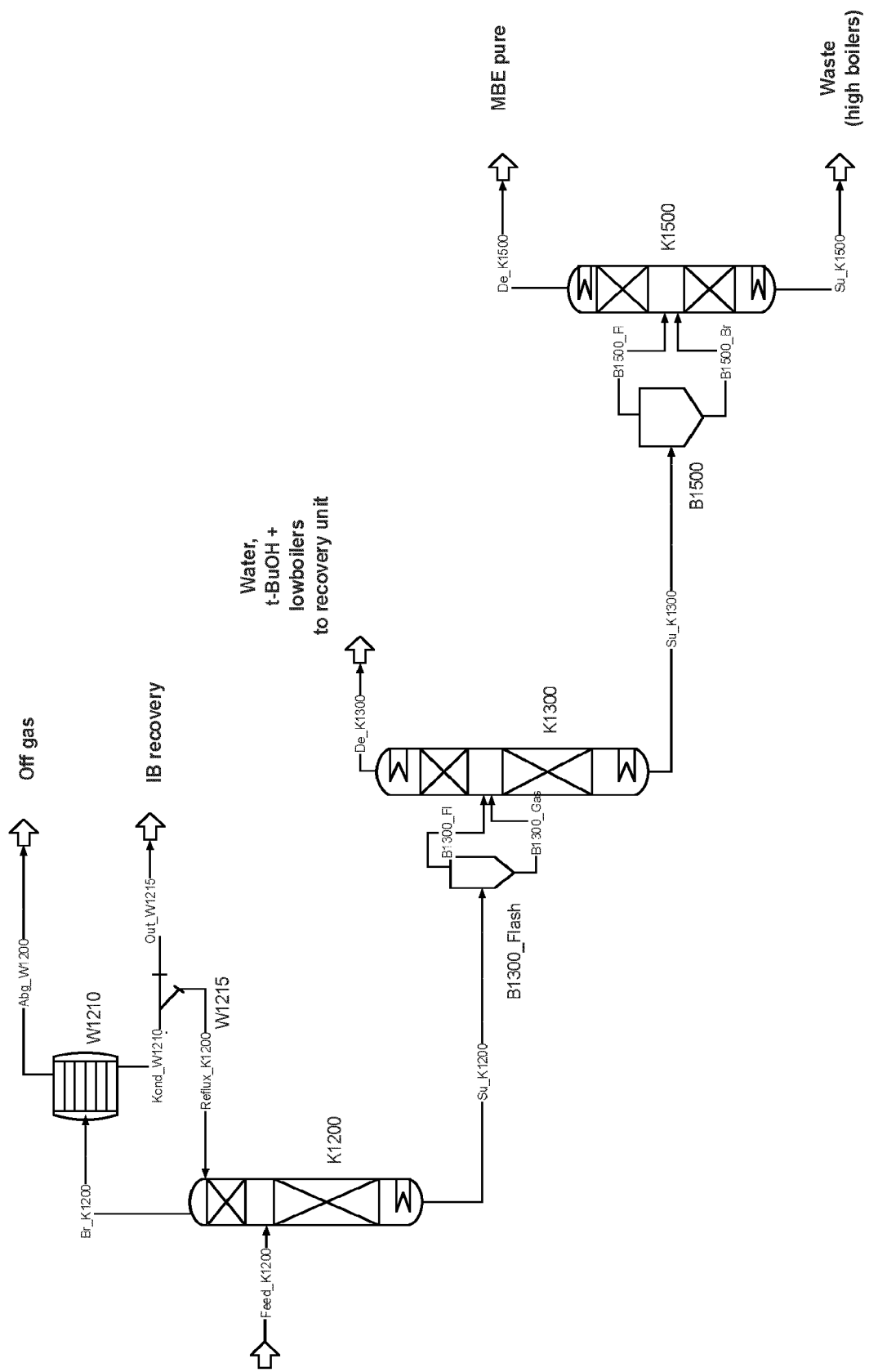
FIG. 2: shows the scheme of the process according to example 2: the MBE recovery from the low boiling solvent tert-butanol, the recovery of isobutene and the recovery of the azeotrope comprising tert-butanol.

WO 2015/067654 A
WO 2014/060259 A
US 2012059177 A
WO 2011/154330 A
WO 2011/147919 A
US 2011054083 A

The invention claimed is:

1. A process for recovering 3-methylbut-3-en-1-ol from a feed stream F1 comprising 3-methylbut-3-en-1-ol, one or more solvents selected from the group consisting of 1-pentanol, 2-hexanol, 2-methyl-hexanol, 4-methyl-hexanol, 3-methyl-hexanol, 3-ethylhexanol, 4-heptanol, 2-methyl-2-heptanol, 3-heptanol, 2-heptanol, 3-ethyl-3-hexanol, 3-methyl-2-heptanol, 2-methyl-4-heptanol, 4-ethyl-4-heptanol, 2-octanol, 2-ethylhexanol, propanediol, glycol, 1,4-butanediol, cyclo-2-penten-1-one, cyclohexanone, cycloheptanone, methanol, ethanol, tert-butanol, 2-propanol, 1-propanol, 2-methyl-2-butanol, isobutanol, 3-pentanol, 1-butanol, 2-pentanol, acetone, 2-butanone, 2-pentanone, ethyl acetate, and acetonitrile, water, and isobutene, the process comprising
  (i) subjecting a feed stream F1 to distillation in a first distillation unit (K1200), obtaining a bottoms stream B1 (Su K1200) comprising 3-methylbut-3-en-1-ol, one or more solvents and water, and a top stream T1 (De K1200) comprising isobutene;
  (ii) subjecting the bottoms stream B1 (Su K1200) to distillation in a second distillation unit (K1300), obtaining a bottoms stream B2 (Su K1300) comprising 3-methylbut-3-en-1-ol and one or more solvents and a top stream T2 (De K1300) comprising water;
  (iii) subjecting the bottoms stream B2 to distillation in a third distillation unit (K1500), obtaining a top stream T3 (De K1500) comprising 3-methylbut-3-en-1-ol and a bottoms stream B3 (Su K1500) comprising one or more solvents;
wherein the bottoms stream B1 (Su K1200) is enriched in methylbut-3-en-1-ol, in the one or more solvents and in water relative to the feed stream F1, wherein the bottoms stream B2 (Su 1300) is enriched in methylbut-3-en-1-ol relative to the bottoms stream B 1, wherein the top stream T3 (De K1500) is enriched in methylbut-3-en-1-ol relative to the bottoms stream B2(Su K1300).

2. The process of claim 1, wherein the feed stream F1 (feed_K1200) is a reaction mixture obtained by a method for preparing of 3-methylbut-3-en-1-ol, said method comprising
  (t) providing a mixture comprising aqueous formaldehyde, isobutene and the one or more solvents;
  (tt) contacting the mixture provided in (t) with a condensation catalyst comprising a zeolitic material, obtaining the feed stream F1;
wherein the framework structure of the zeolitic material in (tt) comprises Si, O, optionally Al, and a tetravalent element Y which is one or more of Sn, Ti and Zr, wherein in the framework structure of the zeolitic material in (tt), the molar Al:Si ratio is in the range of from 0:1 to 0.001:1.

3. The process of claim 1, wherein at least 5 weight % of the feed stream F1 (feed_K1200) consist of methylbut-3-en-1-ol, at least 30 weight % of the feed stream F1 consist of the one or more solvents, at least 20 weight % of the feed stream F1 consist of isobutene and at least 1 weight % of the feed stream F1 consist of water, and wherein at least 96 weight % of the feed stream F1 consist of 3-methylbut-3-en-1-ol, the one or more solvents, water and isobutene, in each case based on the total weight of the feed stream F1.

4. The process of claim 1, wherein at least 10 weight % of the bottoms stream B 1 (Su K1200) consist of methylbut-3-en-1 ol, at least 50 weight % of the bottoms stream B 1 (Su K1200) consist in the one or more solvents, at least 3 weight % of the bottoms stream B 1 (Su K1200) consist of water and less than 0.1 weight % of the bottoms stream B1 consist of isobutene, and wherein at least 96 weight-% of the bottoms stream B1 consist of 3-methylbut-3-en-1-ol, the one or more solvents and water, in each case based on the total weight of the bottoms stream B1.

5. The process of claim 1, wherein the one or more solvents comprised in the feed stream F1 have a boiling point higher than the boiling point of 3-methylbut-3-en-1-ol and wherein the boiling point of 3-methylbut-3-en-1-ol is in the range of from 130 to 132° C. at an absolute pressure of 1 bar.

6. The process of claim 1, wherein the distillation unit according to (i) is a distillation tower, wherein the distillation according to (i) is carried out at a pressure at the top of the tower in the range of from 4 to 15 bar(abs), at a temperature at the bottoms of the tower in the range of from 140 to 190° C., and at a temperature at the top of the tower in the range of from 40 to 80° C., and wherein the tower has from 5 to 40 theoretical plates.

7. The process of claim 1, wherein the distillation unit according to (ii) is a distillation tower wherein the distillation according to (ii) is carried out at a pressure at the top of the tower in the range of from 0.1 to 2 bar(abs), at a temperature at the bottoms of the tower in the range of from 130 to 180° C., and at a temperature at the top of the tower in the range of from 60 to 110° C., wherein the tower has from 15 to 50 theoretical plates, wherein the bottoms stream B2 (Su K1300) is enriched in methylbut-3-en-1-ol and in the one or more solvents relative to the bottoms stream B1 (Su K1200) and wherein at least 10 weight % of the bottoms stream B2 (Su K1300) consist of methylbut-3-en-1-ol, at least 55 weight-%, of the bottoms stream B2 (Su K1300) consist of the one or more solvents, and less than 0.05 weight % of the bottoms stream B2 (Su K1300) consist of water, and wherein at least 96 weight-% of the bottoms stream B2 consist of 3-methylbut-3-en-1-ol and the one or more solvents, in each case based on the total weight of the bottoms stream B2.

8. The process of claim 1, wherein the distillation unit according to (iii) is a distillation tower, wherein the distillation according to (iii) is carried out at a pressure at the top of the tower in the range of from 0.03 to 1.5 bar(abs), at a temperature at the bottoms of the tower in the range of from 90 to 150° C., and at a temperature at the top of the tower in the range of from 45 to 90° C., wherein the tower has from 10 to 45 theoretical plates and wherein the top stream T3 (De K1500) is enriched in methylbut-3-en-1-ol relative to the bottoms stream B2 (Su K1300) and wherein the bottoms stream B3 (Su K1500) is enriched in the one or more solvents relative to the bottoms stream B2 (Su K1300).

9. The process of claim 1, wherein the top stream T2 (De K1300) additionally comprises 3-methylbut-3-en-1-ol, and wherein the process further comprises
(iv) subjecting the top stream T2 (De K1300) to a separation phase (B1310) in a phase separation unit, and obtaining an aqueous liquid stream L2aq (B 1310 WP) comprising water and 3-methylbut-3-en-1-ol and an organic liquid stream L2or (B1310 OP) comprising 3-methylbut-3-en-1-ol and water, wherein the organic liquid stream L2or is richer in 3-methylbut-3-en-1-ol than the aqueous liquid stream L2aq wherein preferably at least 96 weight-% of the 3-methylbut-3-en-1-ol comprised in the top stream T2 is recovered in the organic liquid stream L2or;
and wherein the process further comprises separating a portion PT2 (Reflux_K1300) and a portion L2or' (OP-_Out) of the organic liquid stream L2or (B1310 OP) from the organic liquid stream L2or (B1310 OP) and feeding the portion PT2 back to the top of the distillation tower according to (ii), wherein the portion PT2 is from 94 to 98 weight % of L2or based in the total weight of L2or.

10. The process of claim 8, wherein the process further comprises recovering the one or more solvents comprised in the bottoms stream B3, (Su K1500).

11. The process of claim 1, wherein the one or more solvents comprised in the feed stream F1 have a boiling point lower than the boiling point of 3-methylbut-3-en-1-ol wherein the boiling point of 3-methylbut-3-en-1-ol is in the range of from 130 to 132° C., wherein the boiling points are at an absolute pressure of 1 bar.

12. The process of claim 1, wherein the distillation unit according to (i) is a distillation tower, wherein the distillation according to (i) is carried out at a pressure at the top of the tower in the range of from 4 to 20 bar(abs), at a temperature at the bottoms of the tower in the range of from 130 to 180° C., and at a temperature at the top of the tower in the range of from 40 to 90° C. and wherein the tower has from 7 to 30 theoretical plates.

13. The process of claim 1, wherein the distillation unit according to (ii) is a distillation tower, wherein the distillation according to (ii) is carried out at a pressure at the top of the tower in the range of from 0.05 to 3 bar(abs), at a temperature at the bottoms of the tower in the range of from 130 to 155° C., and at a temperature at the top of the tower in the range of from 60 to 95° C., wherein the tower has from 10 to 50 theoretical plates, wherein at least 84 weight % of the bottoms stream B2 (Su K1300) consist of methylbut-3-en-1-ol, less than 0.25 weight % of the bottoms stream B2 (Su K1300) consist of the one or more solvents, less than 0.3 weight-% of the bottoms stream B2 (Su K1300) consist of water, in each case based on the total weight of the bottoms stream B2.

14. The process of claim 1, wherein the distillation unit according to (iii) is a distillation tower, wherein the distillation according to (iii) is carried out at a pressure at the top of the tower in the range of from 0.03 to 1.4 bar(abs) at a temperature at the bottoms of the tower in the range of from 120 to 170° C., and at a temperature at the top of the tower in the range of from 45 to 95° C., wherein the tower has from 4 to 25 theoretical plates and wherein at least 98 weight-%, weight-% of the top stream T3 (De K1500) consist of 3-methylbut-3-en-1-ol and wherein less than 700 ppm (0.07 weight-%), of the top stream T3 (De K1500) consist of the one or more solvents, in each case based on the total weight of the top stream T3.

15. The process of claim 1, wherein at least 92 weight % of the top stream T1 (Br K1200) consist of isobutene, based on the total weight of the top stream T1 (Br K1200).

16. The process of claim 1, wherein prior to (i) the process comprises
(t) providing a mixture comprising aqueous formaldehyde, isobutene and the one or more solvents;
(tt) contacting the mixture provided in (t) with a condensation catalyst comprising, a heterogeneous catalyst selected from the group consisting of a zeolitic material, a mesoporous silica, a metal oxide or mixed metal oxides supported rare earth metals, and combination of two or more thereof, and obtaining the feed stream F1.

17. The process of claim 16, wherein the zeolitic material is a zeolitic material comprising Si, O, optionally Al, and a tetravalent element Y which is one or more of Sn, Ti and Zr, wherein in the framework structure of the zeolitic material, the molar Al:Si ratio is in the range of from 0:1 to 0.001:1, a metal doped zeolite, a rare-earth metal doped zeolite or an alkaline earth modified Al-containing zeolite.

18. The process of claim 16, wherein the mesoporous silica is a Sn mesoporous silica.

19. The process of claim 16, wherein the metal oxide is silica, alumina, clays, $TiO_2$, $ZnO$, or $ZnO_2$.

* * * * *